(12) United States Patent
Saiga

(10) Patent No.: US 11,241,142 B2
(45) Date of Patent: Feb. 8, 2022

(54) ENDOSCOPE VALVE AND ENDOSCOPE

(71) Applicant: OLYMPUS CORPORATION, Tokyo (JP)

(72) Inventor: Kazuya Saiga, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 294 days.

(21) Appl. No.: 16/525,681

(22) Filed: Jul. 30, 2019

(65) Prior Publication Data

US 2019/0350441 A1    Nov. 21, 2019

Related U.S. Application Data

(63) Continuation of application No. PCT/JP2017/047270, filed on Dec. 28, 2017.

(30) Foreign Application Priority Data

Feb. 1, 2017  (JP) .............................. JP2017-016866

(51) Int. Cl.
*A61B 1/00* (2006.01)
*A61B 1/015* (2006.01)

(52) U.S. Cl.
CPC ...... *A61B 1/00068* (2013.01); *A61B 1/00119* (2013.01); *A61B 1/015* (2013.01)

(58) Field of Classification Search
CPC . A61B 1/00068; A61B 1/00119; A61B 1/015; A61B 1/00094; A61B 5/150221; A61B 2017/3464; A61M 1/774
See application file for complete search history.

(56) References Cited

U.S. PATENT DOCUMENTS

| 4,800,869 A | * | 1/1989 | Nakajima | ............. | A61M 1/774 600/158 |
| 5,391,145 A | * | 2/1995 | Dorsey, III | ........... | A61M 1/774 604/33 |

(Continued)

FOREIGN PATENT DOCUMENTS

| JP | 7-255664 A | 10/1995 |
| JP | 7-275189 A | 10/1995 |

(Continued)

OTHER PUBLICATIONS

International Search Report dated Mar. 20, 2018 received in PCT/JP2017/047270.

*Primary Examiner* — Alexandra L Newton
*Assistant Examiner* — Jae Woo
(74) *Attorney, Agent, or Firm* — Scully, Scott, Murphy & Presser, P.C.

(57) ABSTRACT

An endoscope valve includes: a piston portion; and an attachment member including a surface forming a hollow space extending in a central axis direction. The piston portion includes: protrusions protruding in a direction perpendicular to the central axis and abutting a surface forming the hollow space of the attachment member; and a seal portion formed in a hollow disk shape with the central axis of the piston portion as a symmetry axis and configured to seal a portion between the attachment member and the seal portion. In the protrusions, when a length of the protrusion in a protrusion direction is indicated by $d_A$, a length of the protrusion in the central axis direction is indicated by $d_B$, and a shrinkage amount of the protrusion when the protrusion comes into pressure-contact with a pressure-contact object is indicated by $d_C$, relationships of $d_B \leq d_A$ and $d_C < d_A$ are satisfied.

8 Claims, 46 Drawing Sheets

(56) References Cited

U.S. PATENT DOCUMENTS

| | | | |
|---|---|---|---|
| 5,697,888 A * | 12/1997 | Kobayashi | A61B 1/015 600/159 |
| 5,840,016 A * | 11/1998 | Kitano | A61B 1/00068 600/159 |
| 5,871,441 A * | 2/1999 | Ishiguro | A61B 1/122 600/133 |
| 6,908,429 B2 * | 6/2005 | Heimberger | A61M 1/7413 600/159 |
| 9,307,890 B2 * | 4/2016 | Ouchi | A61B 1/00091 |
| 9,603,509 B2 * | 3/2017 | Ando | A61B 1/015 |
| 10,238,273 B2 * | 3/2019 | Xu | A61B 1/00068 |
| 10,448,814 B2 * | 10/2019 | Rebholz | A61B 1/015 |
| 10,674,898 B2 * | 6/2020 | Anderson | A61B 1/015 |
| D912,245 S * | 3/2021 | Grudo | A61B 1/0011 D24/129 |
| 2012/0088975 A1 * | 4/2012 | Morimoto | A61B 1/015 600/159 |
| 2013/0303844 A1 * | 11/2013 | Grudo | A61B 1/0011 600/101 |
| 2015/0144215 A1 * | 5/2015 | Bellofatto | A61B 1/0011 137/625.69 |
| 2015/0148608 A1 * | 5/2015 | Fukushima | A61B 1/00094 600/116 |
| 2016/0143516 A1 * | 5/2016 | Xu | A61B 1/00068 600/159 |

FOREIGN PATENT DOCUMENTS

| | | | |
|---|---|---|---|
| JP | 10-028670 A | | 2/1998 |
| JP | 2001-258825 A | | 9/2001 |
| JP | 2001258825 A | * | 9/2001 |
| JP | 2007-111266 A | | 5/2007 |
| JP | 2012-254136 A | | 12/2012 |
| JP | 2013-116144 A | | 6/2013 |

* cited by examiner (a)  (b)

ENDOSCOPE VALVE AND ENDOSCOPE

This application is a continuation of PCT International Application No. PCT/JP2017/047270 filed on Dec. 28, 2017, which designates the United States, incorporated herein by reference, and which claims the benefit of priority from Japanese Patent Application No. 2017-016866, filed on Feb. 1, 2017, incorporated herein by reference.

BACKGROUND

The present disclosure relates to an endoscope valve and an endoscope.

In the related art, an ultrasound endoscope, which observes an inside of a subject by inserting a flexible and elongated insertion portion into the subject such as a human and transmitting and receiving ultrasonic waves using an ultrasound transducer provided on a distal end side of the insertion portion, known. In the ultrasound endoscope, a plurality of conduits through which a fluid may flow, a cylinder which communicates with the plurality of conduits, and a piston (an endoscope air/water supply valve) which is attached to the cylinder and switches a connection state of the plurality of conduits according to a pressing operation are provided. For example, in an endoscope disclosed in JP H10-28670 A, an endoscope air/water supply valve is disclosed, which includes a seal member which protrudes in a direction substantially orthogonal to a forward or rearward movement direction to airtightly or watertightly seal a portion between a cylinder and the seal member. In JP H10-28670 A, the seal member comes into pressure contact with a wall surface of the cylinder to airtightly or watertightly seal a space in the endoscope, and thus, a flow path is formed.

SUMMARY

According to one aspect of the present disclosure, there is provided an endoscope valve for switching connection states of a plurality of conduits formed in an endoscope, the endoscope valve including: a piston portion having a rod shape extending along a central axis; and an attachment member including a surface forming a hollow space extending in a central axis direction, the attachment member being inserted into the piston portion and attachable to the endoscope, wherein the piston portion includes: a plurality of protrusions protruding in a direction perpendicular to the central axis and abutting a surface forming the hollow space of the attachment member; and a seal portion formed in a hollow disk shape with the central axis of the piston portion as a symmetry axis and configured to seal a portion between the attachment member and the seal portion, and in the plurality of protrusions, when a length of the protrusion in a protrusion direction is indicated by $d_A$, a length of the protrusion in the central axis direction is indicated by $d_B$, and a shrinkage amount of the protrusion when the protrusion comes into pressure-contact with a pressure-contact object is indicated by $d_C$, relationships of $d_B \leq d_A$ and $d_C < d_A$ are satisfied.

The above and other features, advantages and technical and industrial significance of this disclosure will be better understood by reading the following detailed description of presently preferred embodiments of the disclosure, when considered in connection with the accompanying drawings.

DETAILED DESCRIPTION

Hereinafter, a mode (hereinafter, referred to as an "embodiment") for carrying out the present disclosure will be described with reference to the attached drawings.

Figure 1:
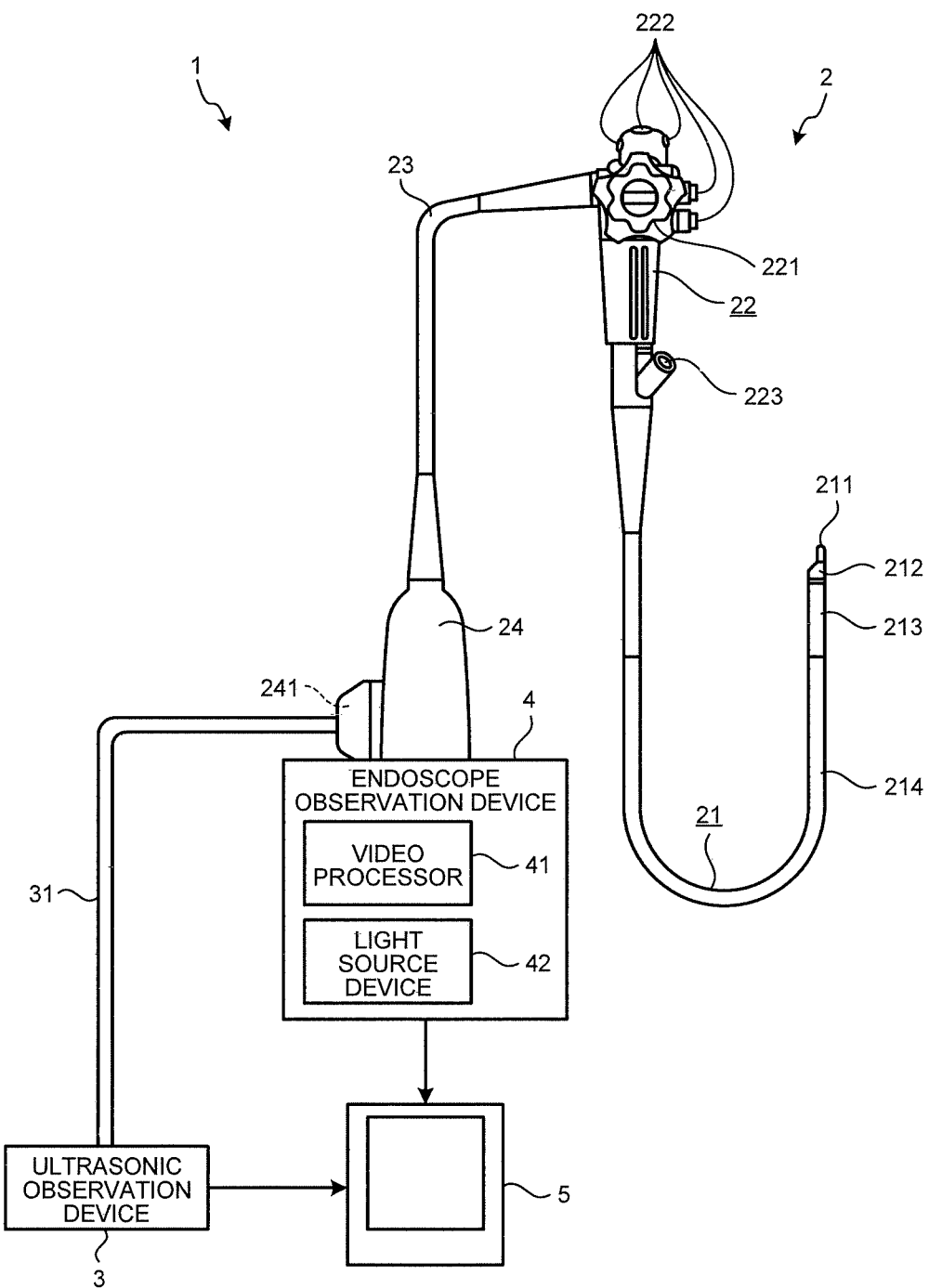
FIG. 1 is a view schematically illustrating an endoscope system according to an embodiment.

FIG. 1 is a view schematically illustrating an endoscope system 1 according to the embodiment. The endoscope system 1 illustrated in FIG. 1 is a system for performing an ultrasonic diagnosis in a subject of a person or the like using an ultrasound endoscope. As illustrated in FIG. 1, the endoscope system 1 includes an ultrasound endoscope 2, an ultrasonic observation device 3, an endoscope observation device 4, and a display device 5.

The ultrasound endoscope 2 has a function as an endoscope according to the present disclosure. A portion of the ultrasound endoscope 2 may be inserted into the subject, and the ultrasound endoscope 2 has a function of transmitting an ultrasonic wave pulse toward a body wall in the subject, receiving an ultrasonic echo reflected by the subject, and outputting an echo signal, and a function of outputting an image signal by capturing an inside of the subject. In addition, a detailed configuration of the ultrasound endoscope 2 will be described later.

The ultrasonic observation device 3 is electrically connected to the ultrasound endoscope 2 via an ultrasonic cable 31 and outputs a pulse signal to the ultrasound endoscope 2 via the ultrasonic cable 31, and an echo signal is input to the ultrasonic observation device 3 from the ultrasound endoscope 2. Then, in the ultrasonic observation device 3, predetermined processing is performed on the echo signal to generate an ultrasound image.

An endoscope connector 24 described later of the ultrasound endoscope 2 is detachably connected to the endoscope observation device 4. As illustrated in FIG. 1, the endoscope observation device 4 includes a video processor 41 and a light source device 42.

An image signal from the ultrasound endoscope 2 is input to the video processor 41 via the endoscope connector 24. In addition, the video processor 41 performs predetermined processing on the image signal to generate an endoscope image.

The light source device 42 supplies illumination light for illuminating the inside of the subject via the endoscope connector 24 to the ultrasound endoscope 2.

The display device 5 is constituted by liquid crystal or organic Electro Luminescence (EL), and displays the ultrasound image generated by the ultrasonic observation device 3, the endoscope image generated by the endoscope observation device 4, or the like.

Next, a configuration of the ultrasound endoscope 2 will be described with reference to FIGS. 1 to 3. As illustrated in FIG. 1, the ultrasound endoscope 2 includes an insertion portion 21, an operating unit 22, a universal cable 23, and the endoscope connector 24. In addition, a "distal end side" described below means a distal end side (a distal end side in an insertion direction into the subject) of the insertion portion 21. In addition, a "proximal end side" described below means a side away from the distal end of the insertion portion 21.

The insertion portion 21 is a portion to be inserted into the subject. As illustrated in FIG. 1, the insertion portion 21 includes an ultrasound probe 211 which is provided on the distal end side, a rigid member 212 which extends to a proximal end side of the ultrasound probe 211, a bending portion 213 which is connected to a proximal end side of the rigid member 212 and may be curved, and a flexible tube 214 which is connected to a proximal end side of the bending portion 213 and has flexibility.

Here, a light guide (not illustrated) for transmitting the illumination light supplied from the light source device 42 and a plurality of signal cables (not illustrated) for transmitting the above-described pulse signal, echo signal, and image signal are routed inside the insertion portion 21, the operating unit 22, the universal cable 23, and the endoscope connector 24. In addition, a detailed configuration (ultrasound probe 211 and rigid member 212) of the distal end side of the insertion portion 21 will be described later.

The operating unit 22 is connected to a proximal end of the insertion portion 21 and receives various operations from a doctor or the like. As illustrated in FIG. 1, the operating unit 22 includes a bending knob 221 for bending the bending portion 213 and a plurality of operating members 222 for performing various operations.

Here, distal end side first to fifth conduits 61 to 65 (refer to FIG. 3) are provided in the insertion portion 21 and the operating unit 22. In addition, first and second cylinders 7 and 8 (refer to FIG. 3) which communicate with the distal end side first to fifth conduits 61 to 65 are provided in the operating unit 22. The first cylinder 7 functions as an air/water supply cylinder. The second cylinder 8 functions as a suction cylinder. In addition, an air/water supply button 9 and a suction button 10 (refer to FIG. 41 or the like) are respectively attached to the first and second cylinders 7 and 8, and each of the air/water supply button 9 and the suction button 10 is a conduit switching valve which constitutes a portion of the plurality of operating member 222 and switches connection states between the distal end side first to fifth conduits 61 to 65 and proximal end side first to third conduits 66 to 68 (refer to FIG. 3) described later according to the operation from the doctor or the like. In addition, the air/water supply button 9 corresponds to an endoscope air/water supply valve according to the present disclosure. The detailed configurations of the plurality of conduits 6 will be described later. In addition, connection states of the plurality of conduits 6 in accordance with operations of the air/water supply button 9 and the suction button 10 will be described later. As structures of the second cylinder 8 and the suction button 10, a known structure (for example, JP 2007-111266A) may be adopted. Therefore, hereinafter, descriptions of the detailed structures of the second cylinder 8 and the suction button 10 are omitted, and the connection states of the plurality of conduits 6 in accordance with the operations of the air/water supply button 9 and the suction button 10 will be described with reference to FIG. 41 or the like.

The universal cable 23 is a cable which extends from the operating unit 22 and in which the above-described light guide (not illustrated) and plurality of signal cables (not illustrated) are disposed.

The endoscope connector 24 is provided on an end portion of the universal cable 23. In addition, the endoscope connector 24 includes an ultrasonic connector 241 (refer to FIG. 3) to which the ultrasonic cable 31 is connected and a plug portion 242 (refer to FIG. 3) which is inserted into the endoscope observation device 4 and is connected to the video processor 41 and the light source device 42.

Here, the proximal end side first to third conduits 66 to 68 (refer to FIG. 3) which communicate with the first and second cylinders 7 and 8 provided in the operating unit 22 are provided in the operating unit 22, the universal cable 23, and the endoscope connector 24.

In addition, a plurality of electrical contacts (not illustrated), a light guide base 243 (refer to FIG. 3), and an air supply base 244 (refer to FIG. 3) are provided in the plug portion 242. The plurality of electrical contacts are portions which are electrically connected to the video processor 41 when the endoscope connector 24 is inserted into the endoscope observation device 4.

The light guide base 243 is a portion into which an incident end side of the above-described light guide (not illustrated) is inserted and which optically connects the light guide and the light source device 42 to each other when the endoscope connector 24 is inserted into the endoscope observation device 4.

The air supply base 244 is a portion which is connected to a light source pump P1 (refer to FIG. 3) which is provided inside the light source device 42 when the endoscope connector 24 is inserted into the endoscope observation device 4.

In addition, first and second water supply bases 245 and 246 (refer to FIG. 3) to which an external water supply tank Ta (refer to FIG. 3) is connected and a suction base 247 (refer to FIG. 3) to which an external suction pump P2 (refer to FIG. 3) is connected are provided in the endoscope connector 24.

Figure 2:
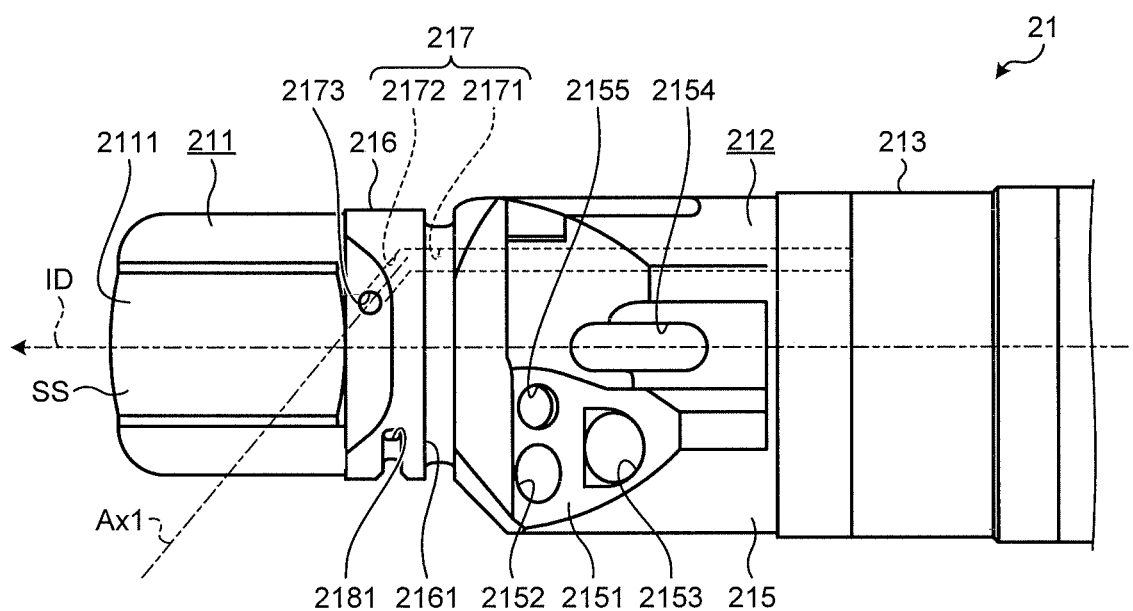
FIG. 2 is an enlarged view illustrating a distal end side of an insertion portion.
Figure 3:
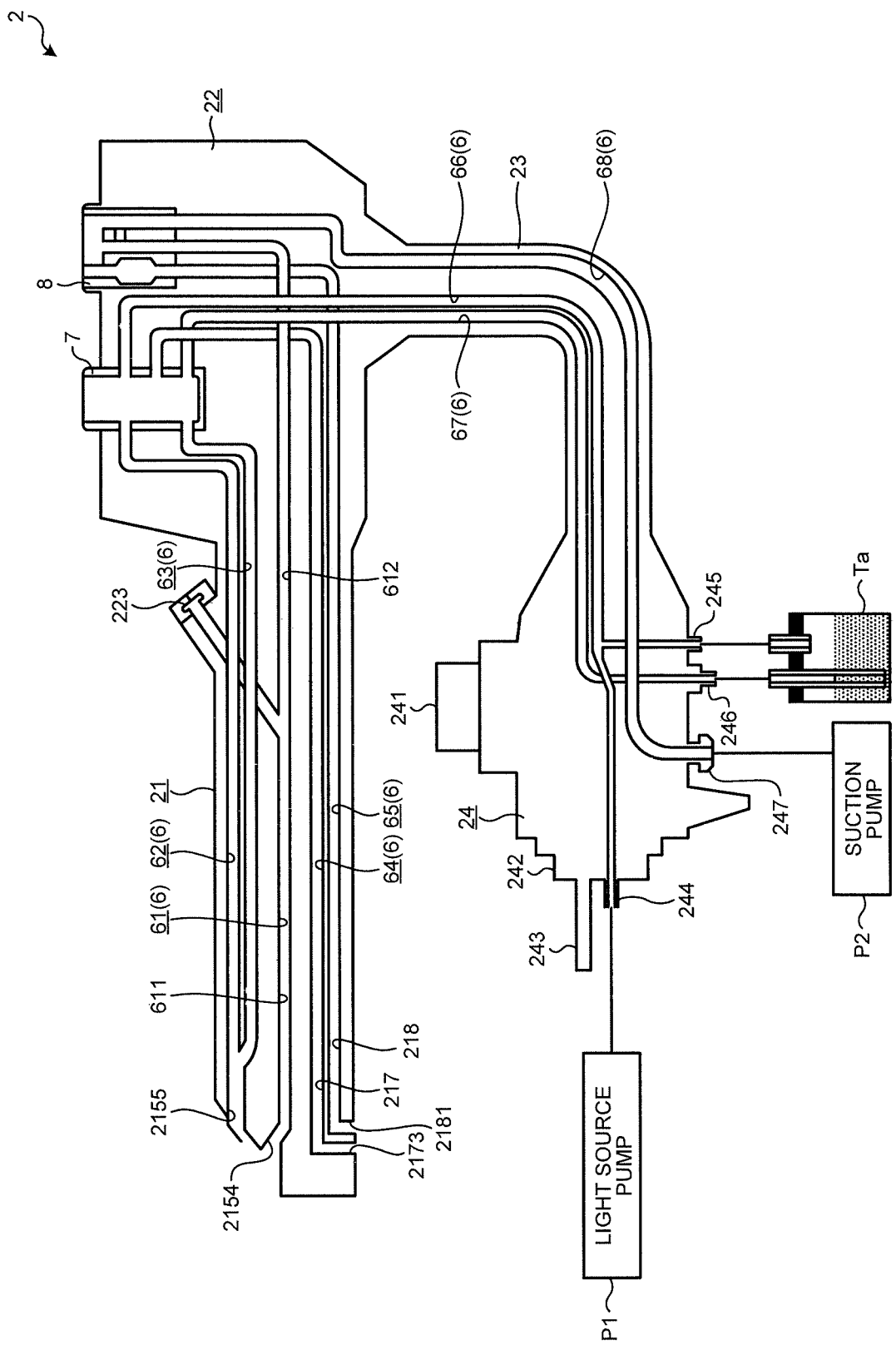
FIG. 3 is a view schematically illustrating a plurality of conducts which are provided in an ultrasound endoscope.

FIG. 2 is an enlarged view of the distal end portion of the insertion portion 21. Specifically, FIG. 2 is a view when the distal end side of the insertion portion 21 is viewed from a top side (in a direction orthogonal to an insertion direction ID of the insertion portion 21 and a scanning surface SS of a transducer unit 2111).

Hereinafter, configurations of the ultrasound probe 211 and the rigid member 212 will be described in order with reference to FIG. 2.

The ultrasound probe 211 has the transducer unit 2111 in which a plurality of ultrasound transducers are regularly arranged. Here, the ultrasound transducer has an acoustic lens, a piezoelectric element, and a matching layer, and acquires an ultrasonic echo which contributes to an ultrasonic tomographic image inside the body wall in the subject. In addition, the transducer unit 2111 converts the pulse signal input from the ultrasonic observation device 3 via the above-described signal cable (not illustrated) into the ultrasonic pulse and transmits the converted ultrasonic pulse into the subject. In addition, the transducer unit 2111 converts the ultrasonic echo reflected in the subject into an electrical echo signal, and outputs the converted echo signal to the ultrasonic observation device 3 via the above-described signal cable (not illustrated).

In the present embodiment, the transducer unit 2111 is formed in a convex shape, and a plurality of ultrasound transducers are regularly disposed so as to form a convex arc and have a scanning surface SS having an arc shape in cross section. That is, the transducer unit 2111 may scan ultrasonic waves in a fan shape extending in a normal direction of the scanning surface SS.

The rigid member 212 is a hard member made of a resin material. The rigid member 212 includes a large diameter portion 215 and a small diameter portion 216.

The large diameter portion 215 is a portion to which the bending portion 213 is connected, and has a substantially columnar shape extending along the insertion direction ID of the insertion portion 21. In addition, a tapered surface 2151 which gradually reduces a diameter of the large diameter portion 215 toward the distal end side is formed on an upper side of the large diameter portion 215. In addition, as illustrated in FIG. 2, in the large diameter portion 215, an illumination hole 2152, a capturing hole 2153, a treatment instrument channel 2154, and an air/water supply hole 2155 penetrating respectively from a proximal end of the large diameter portion 215 to the tapered surface 2151 are formed.

An emission end side of the above-described light guide (not illustrated) is inserted into the inside of the illumination hole 2152. In addition, the inside of the subject is irradiated with illumination light supplied from the light source device 42 via the illumination hole 2152.

An objective optical system (not illustrated) which condenses light (object image) which is emitted from the light source device 42 and reflected in the subject, and an imaging element (not illustrated) which captures the object image condensed by the objective optical system are disposed inside the capturing hole 2153. In addition, the image signal captured by the imaging element is transmitted to the endoscope observation device 4 (video processor 41) via the above-described signal cable (not illustrated).

The treatment instrument channel 2154 constitutes a portion of the distal end side first conduit 61.

The air/water supply holes 2155 form a portion of the distal end side second and third conduits 62 and 63.

The small diameter portion 216 has a substantially columnar shape (substantially columnar shape having an outer diameter smaller than that of the large diameter portion 215) extending along the insertion direction ID of the insertion portion 21, and is integrally formed at the distal end of the large diameter portion 215. A balloon attachment groove 2161 for attaching a balloon (not illustrated) which may be expanded or shrunk and of which inside is filled with water is formed on a periphery on the proximal end side of the small diameter portion 216. When the balloon is attached, an ultrasound probe 211 is inserted into the inside of the balloon from the mouth portion (the mouth portion for causing degassed water to flow into the inside of the balloon) of the balloon. Then, the mouth portion of the balloon is hooked on the balloon attachment groove 2161. In this state, the entire ultrasound probe 211 is covered with the balloon.

In addition, as illustrated by broken lines, a water supply hole 217 penetrating from the proximal end of the large diameter portion 215 to an outer peripheral surface on an upper side of the small diameter portion 216 is formed in the large diameter portion 215 and the small diameter portion 216. The water supply hole 217 includes a first water supply hole 2171 extending from the proximal end of the large diameter portion 215 to the small diameter portion 216 along the insertion direction ID of the insertion portion 21, and a second water supply hole 2172 which communicates with the first water supply hole 2171, extends to be bent with respect to the first water supply hole 2171, and penetrates the outer peripheral surface on the upper side of the small diameter portion 216. Hereinafter, in the second water supply hole 2172, a through hole penetrating the outer peripheral surface on the upper side of the small diameter portion 216 will be referred to as a scanning surface supply port 2173.

More specifically, as illustrated in FIG. 2, in a case where the distal end of the insertion portion 21 is viewed from above, the water supply hole 217 is formed such that a portion of a supply central axis Ax1 (hereinafter, simply referred to as a central axis Ax1) which passes through the scanning surface supply port 2173 and extends a central axis of the second water supply hole 2172 is located in the scanning surface SS. In addition, as illustrated in FIG. 2, in the case where the distal end of the insertion portion 21 is viewed from above, the water supply hole 217 is formed such that the scanning surface supply port 2173 is located at a position deviated from an axis passing through a center in a width direction of the scanning surface SS and the central axis Ax1 intersects the insertion direction ID of the insertion portion 21 at an acute angle. Moreover, in the case where the distal end of the insertion portion 21 is viewed from above, the water supply hole 217 is formed such that the central axis Ax1 intersects a scanning central axis, which passes through an apex of the scanning surface SS and extends in a normal direction of the scanning surface SS, at an acute angle. In addition, the water supply hole 217 is formed such that the scanning surface supply port 2173 is located on the distal end side from the balloon attachment groove 2161. The above-described water supply hole 217 constitutes a portion of a distal end side fourth conduit 64.

In addition, in the large diameter portion 215 and the small diameter portion 216, a suction hole 218 (refer to FIG. 3) which penetrates from the proximal end of the large diameter portion 215 to an outer peripheral surface on a side of the small diameter portion 216 is formed. In addition, in FIG. 2, for convenience of explanation, in the suction hole 218, only a through hole 2181 (hereinafter, referred to as a suction port 2181) penetrating the outer peripheral surface on the side of the small diameter portion 216 is illustrated. Specifically, as illustrated in FIGS. 2 and 3, the suction hole 218 is formed such that the suction port 2181 is located on the distal end side from the balloon attachment groove 2161. The above-described suction hole 218 constitutes a portion of the distal end side fifth conduit 65.

Subsequently, a configuration of the plurality of conduits 6 formed in the ultrasound endoscope 2 will be described with reference to FIG. 3. FIG. 3 is a view schematically illustrating a plurality of conduits 6 which are provided in the ultrasound endoscope 2.

As described above, the plurality of conduits 6 include the distal end side first to fifth conduits 61 to 65 and the proximal end side first to third conduits 66 to 68.

The distal end side first conduit 61 is a conduit for causing a treatment instrument (for example, a puncture needle or the like) to protrude from the treatment instrument channel 2154 to the outside, and is a conduit for sucking a liquid in the subject from the treatment instrument channel 2154. As illustrated in FIG. 3, the distal end side first conduit 61 includes a treatment instrument tube 611 and a suction tube 612.

The treatment instrument tube 611 is routed inside the bending portion 213 and the flexible tube 214, and one end of the treatment instrument tube 611 communicates with the treatment instrument channel 2154. In addition, the treatment instrument tube 611 communicates with a treatment instrument insertion port 223 provided in the operating unit 22. That is, the treatment instrument (for example, the puncture needle or the like) is inserted into the treatment instrument tube 611 via the treatment instrument insertion port 223, and protrudes outside from the treatment instrument channel 2154.

The suction tube 612 is routed inside the operating unit 22, one end of the suction tube 612 communicates with the other end of the treatment instrument tube 611, and the other end of the suction tube 612 communicates with the second cylinder 8.

The distal end side second conduit 62 is a conduit for supplying air from the air/water supply hole 2155 toward a capturing hole (not illustrated) and is routed inside the bending portion 213, the flexible tube 214, and the operating unit 22, and one end of the distal end side second conduit 62 communicates with the air/water supply hole 2155 and the other end thereof communicates with the first cylinder 7.

The distal end side third conduit 63 is a conduit for supplying water from the air/water supply hole 2155 toward the capturing hole (not illustrated) and is routed inside the bending portion 213, the flexible tube 214, and the operating unit 22, and one end of the distal end side third conduit 63 communicates with the air/water supply hole 2155 and the other end thereof communicates with the first cylinder 7.

The distal end side fourth conduit 64 is a conduit for filling the inside of the balloon (not illustrated) from the water supply hole 217 with water and is routed inside the bending portion 213, the flexible tube 214, and the operating unit 22, and one end of the distal end side fourth conduit 64 communicates with the first water supply hole 2171 and the other end thereof communicates with the first cylinder 7.

The distal end side fifth conduit 65 is a conduit for sucking water in the balloon (not illustrated) from the suction hole 218 and is routed inside the bending portion 213, the flexible tube 214, and the operating unit 22, and one end of the distal end side fifth conduit 65 communicates with the suction port 2181 and the other end thereof communicates with the second cylinder 8.

The proximal end side first conduit 66 is a conduit which causes the air discharged from the light source pump P1 to flow to the first cylinder 7 and the water supply tank Ta, and is routed inside the operating unit 22, the universal cable 23, and the endoscope connector 24. Moreover, in the proximal end side first conduit 66, one end branched into two communicates with the air supply base 244 and the first water supply base 245, and the other end communicates with the first cylinder 7.

The proximal end side second conduit 67 is a conduit which causes the water discharged from the water supply tank Ta to flow to the first cylinder 7 and is routed inside the operating unit 22, the universal cable 23, and the endoscope connector 24. In addition, one end of the proximal end side second conduit 67 communicates with the second water supply base 246 and the other end thereof communicates with the first cylinder 7.

The proximal end side third conduit 68 is a conduit for suctioning a liquid in the second cylinder 8 and is routed to inside the operating unit 22, the universal cable 23, and the endoscope connector 24, and one end of the proximal end side third conduit 68 communicates with the suction base 247 and the other end thereof communicates with the second cylinder 8.

Figure 4:
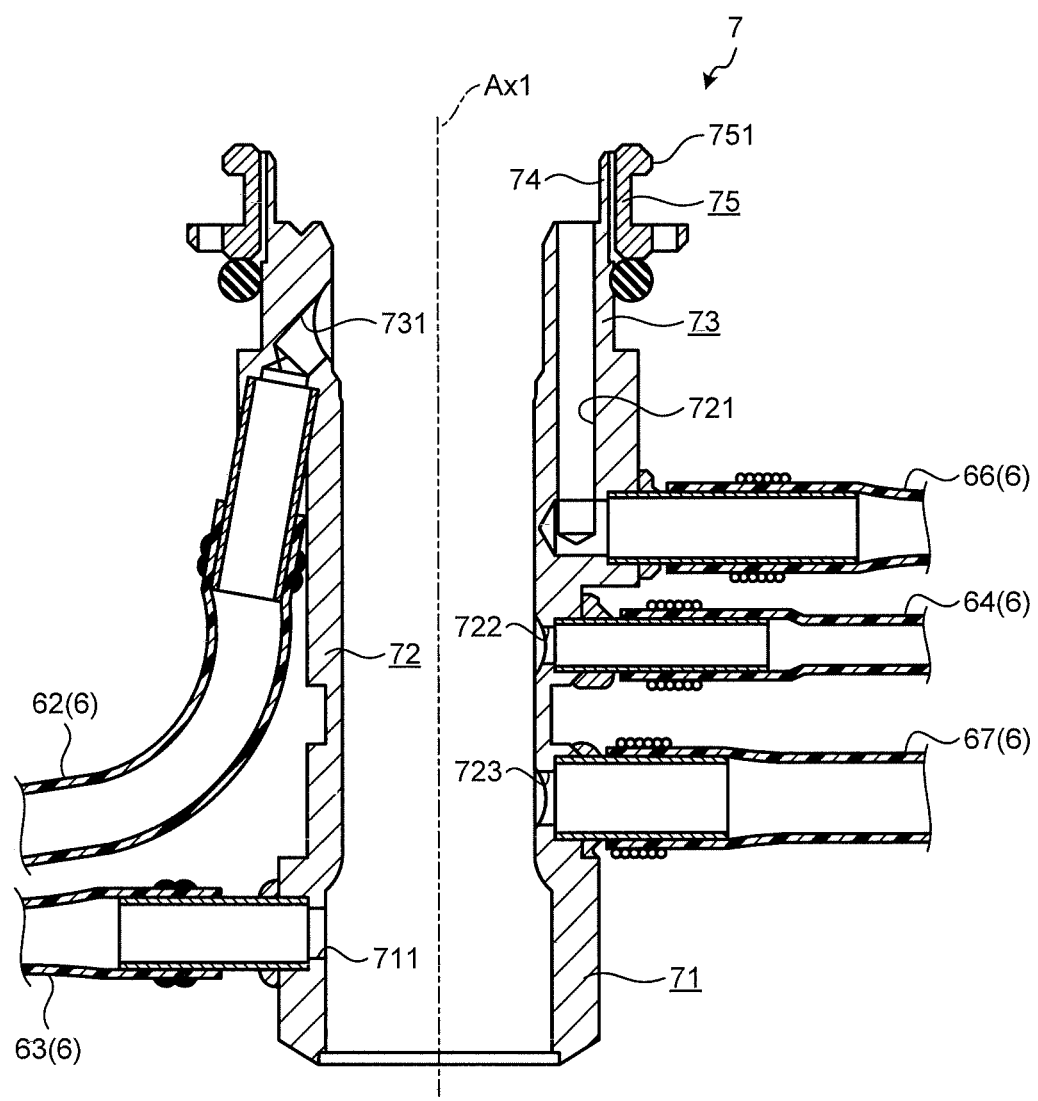
FIG. 4 is a cross-sectional view illustrating a configuration of a first cylinder.

Next, a configuration of the first cylinder 7 will be described with reference to FIG. 4. FIG. 4 is a cross-sectional view illustrating the configuration of the first cylinder 7. The first cylinder 7 has a bottomed cylindrical shape having a central axis Ax1 extending in an upward-downward direction in FIG. 4 as a central axis. In addition, as illustrated in FIG. 4, the first cylinder 7 has a configuration in which a lower end tubular portion 71, a sliding tubular portion 72, an upper end tubular portion 73, and a fitting tubular portion 74 are continuously provided in order from a lower side (a bottom side of the bottomed cylindrical first cylinder 7) toward an upper side (an aperture side of the bottomed cylindrical first cylinder 7) along the central axis Ax1.

A communication passage 711 which communicates with an inside and an outside of the lower end tubular portion 71 is formed on a side wall of the lower end tubular portion 71. In addition, as illustrated in FIG. 4, the other end of the distal end side third conduit 63 is connected to the communication passage 711 via a base or the like.

The sliding tubular portion 72 has an inner diameter smaller than an inner diameter of the lower end tubular portion 71. As illustrated in FIG. 4, communication passages 721 to 723 which communicate with an inside and an outside of the first cylinder 7 are formed on a side wall of the sliding tubular portion 72 in order from the upper side to the lower side. The other end of the proximal end side first conduit 66 is connected to the communication passage 721 via a base or the like. In addition, the other end of the distal end side fourth conduit 64 is connected to the communication passage 722 via a base or the like. Moreover, the other end of the proximal end side second conduit 67 is connected to the communication passage 723 via a base or the like. In addition, as illustrated in FIG. 4, the communication passage 721 is bent upward in the side wall of the sliding tubular portion 72, and then is open at an upper end surface of the upper end tubular portion 73.

The upper end tubular portion 73 has an inner diameter larger than the inner diameter of the sliding tubular portion 72. As illustrated in FIG. 4, a communication passage 731 which communicates with an inside and an outside of the upper end tubular portion 73 is formed on a side wall of the upper end tubular portion 73. In addition, the other end of the distal end side second conduit 62 is connected to the communication passage 731.

The fitting tubular portion 74 has an inner diameter larger than the inner diameter of the upper end tubular portion 73. Further, as illustrated in FIG. 4, a base portion 75 for attaching an air/water supply button 9 is fixed to an outer peripheral surface of the fitting tubular portion 74.

The base portion 75 has a cylindrical shape and is fixed to the outer peripheral surface of the fitting tubular portion 74 by screwing, for example. In addition, the base portion 75 protrudes from the inside of the operating unit 22 to the outside thereof in a state of being fixed to the outer peripheral surface of the fitting tubular portion 74. As illustrated in FIG. 4, an outer peripheral surface of the base portion 75 has an annular shape extending over the entire periphery of the outer peripheral surface, and an engagement protrusion portion 751 which extends from an upper end of the outer peripheral surface to a side away from the central axis Ax1 is provided on the outer peripheral surface of the base portion 75.

Figure 5:
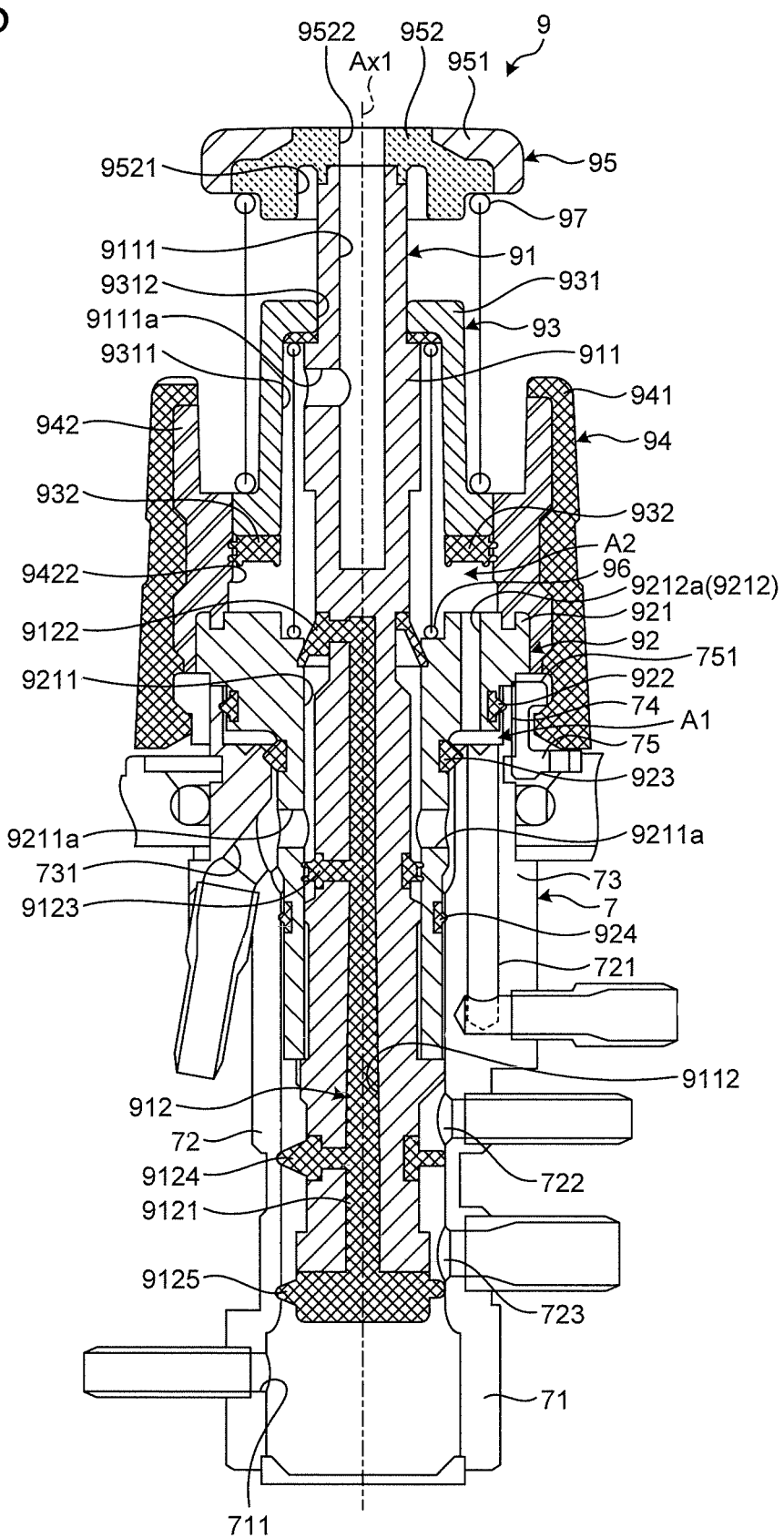
FIG. 5 is a cross-sectional view illustrating a state where an air/water supply button is mounted on a base portion (air/water supply cylinder)
Figure 6:
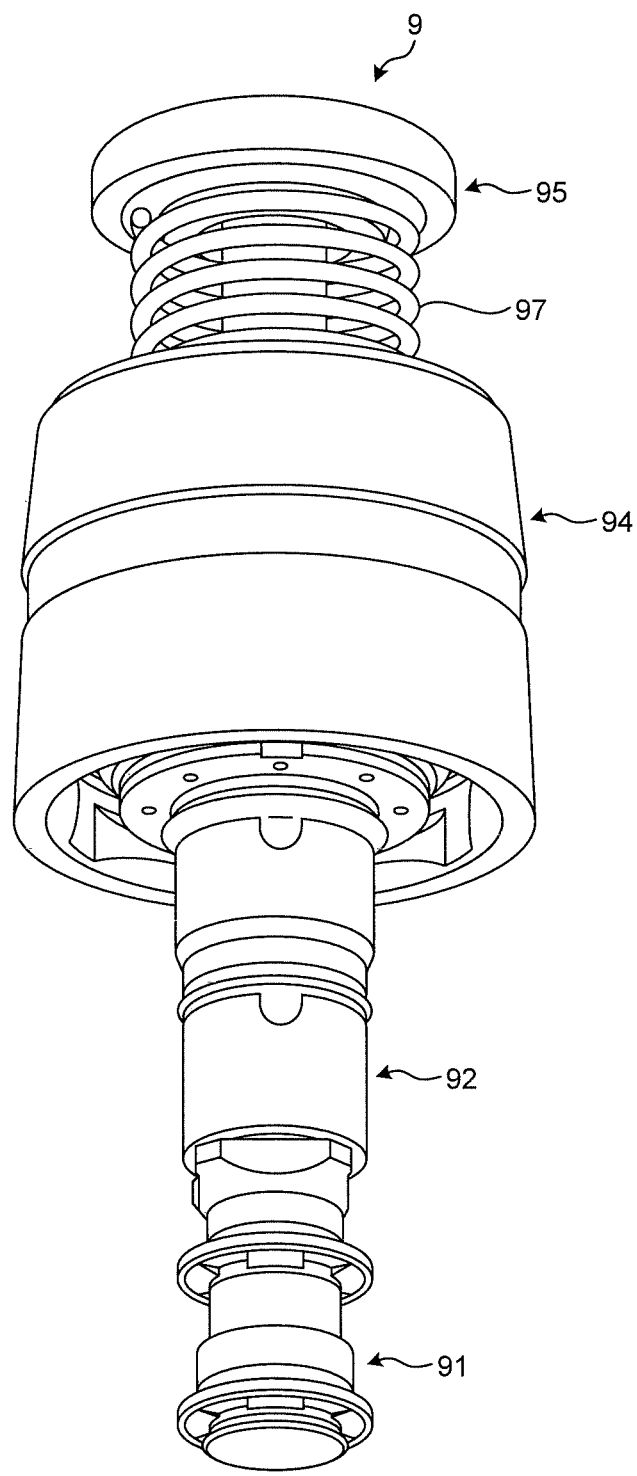
FIG. 6 is a perspective view illustrating a configuration of the air/water supply button.
Figure 7:
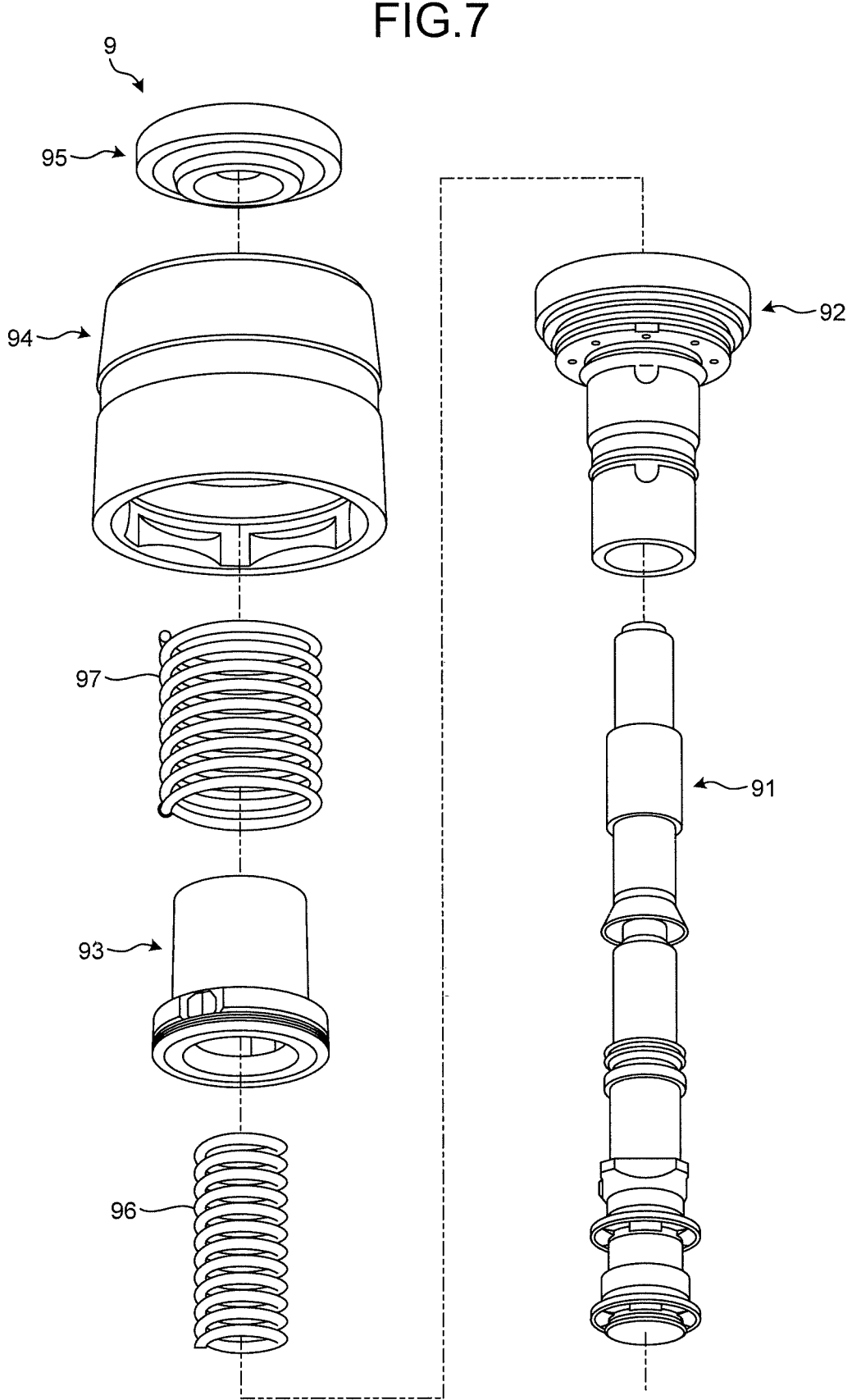
FIG. 7 is a perspective exploded view illustrating the configuration of the air/water supply button.

Next, a configuration of the air/water supply button 9 will be described with reference to FIGS. 5 to 28. FIG. 5 is a view illustrating the configuration of the air/water supply button 9. Specifically, FIG. 5 is a cross-sectional view illustrating a state where the air/water supply button 9 is mounted on the base portion 75 (the first cylinder 7). That is, a lower side in FIG. 5 illustrates a distal end side in a mounting direction of the air/water supply button 9 to the base portion 75. FIG. 5 is a cross-sectional view in which a plane which is broken at an angle of 90° at the central axis Ax1 is a cut surface. FIG. 6 is a perspective view illustrating the configuration of the air/water supply button 9. FIG. 7 is a perspective exploded view illustrating the configuration of the air/water supply button 9.

The air/water supply button 9 includes a shaft portion 91, a first member 92, a second member 93, an attachment member 94, a cap 95, a first coil spring 96, and a second coil spring 97. For example, each member is manufactured by insert molding or outsert molding. The shaft portion 91, the first member 92, the second member 93, and the first coil spring 96 constitute a piston portion. The second member 93 corresponds to a tubular portion.

Figure 8:
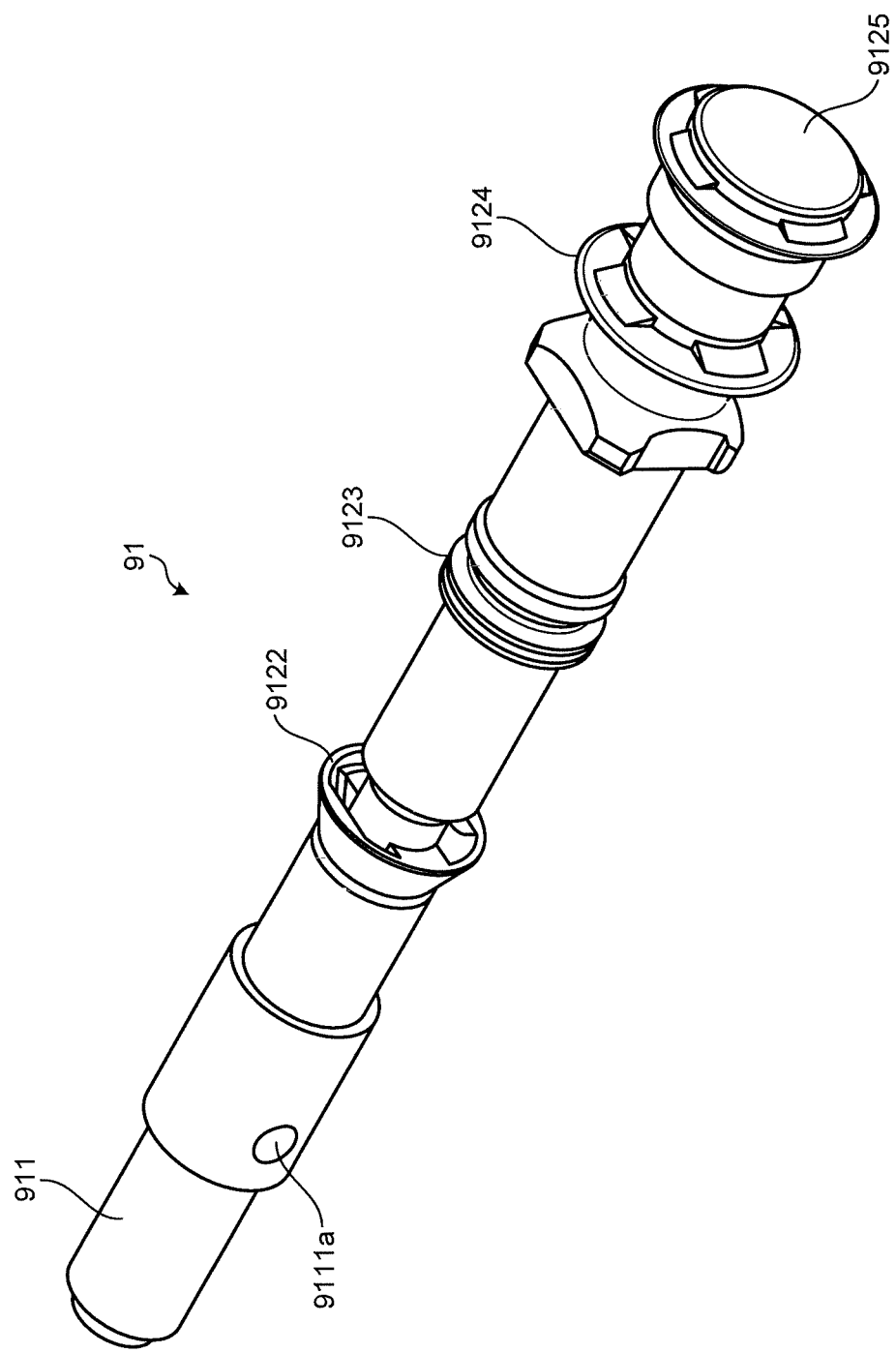
FIG. 8 is a view for explaining a configuration of a main portion of the air/water supply button and is a perspective view illustrating a configuration of a shaft portion.
Figure 9:
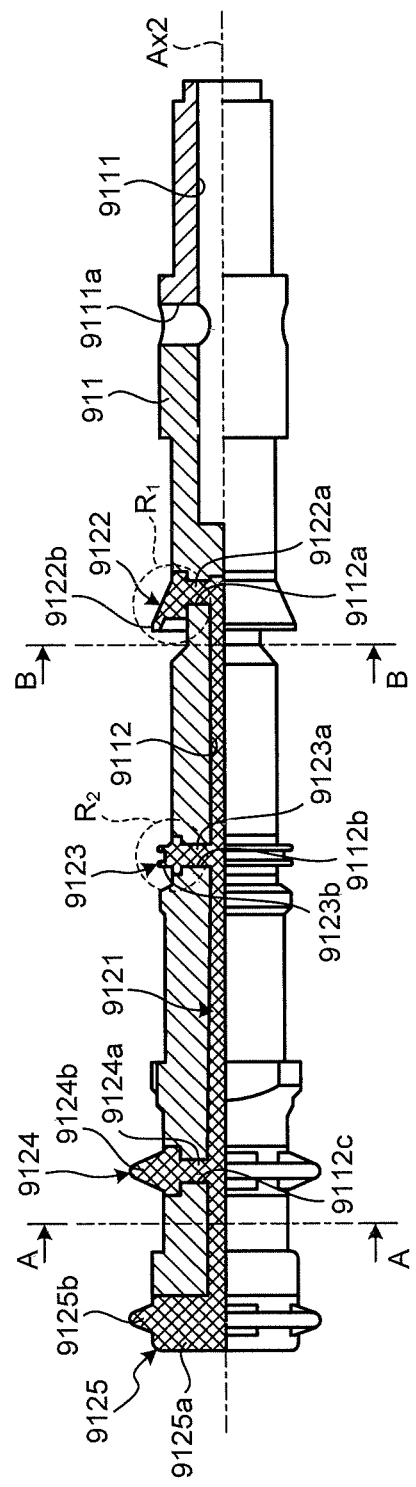
FIG. 9 is a view for explaining the configuration of the main portion of the air/water supply button, and is a partially cross-sectional view illustrating the configuration of the shaft portion.
Figure 10:
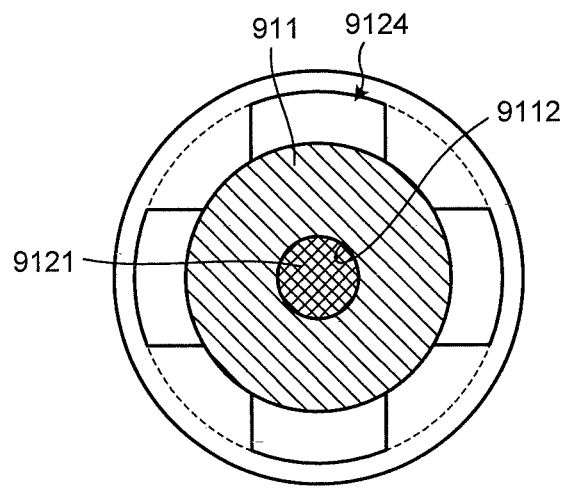
FIG. 10 is a cross-sectional view taken along line A-A illustrated in FIG. 9.
Figure 11:
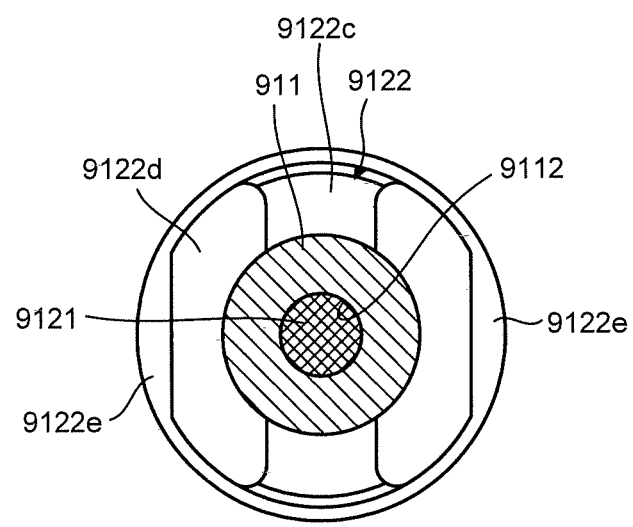
FIG. 11 is a cross-sectional view taken along line B-B illustrated in FIG. 9.
Figure 12:
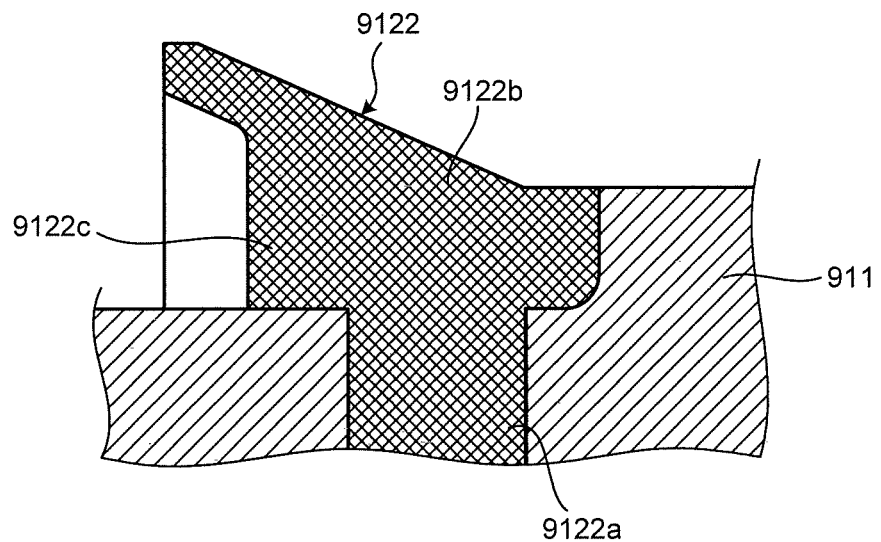
FIG. 12 is an enlarged view of a region $R_1$ illustrated in FIG. 9.
Figure 13:
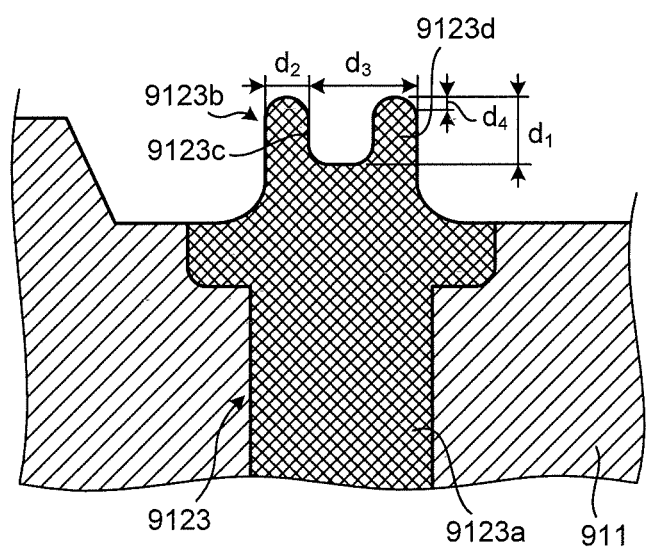
FIG. 13 is an enlarged view of a region $R_2$ illustrated in FIG. 9.
Figure 14:
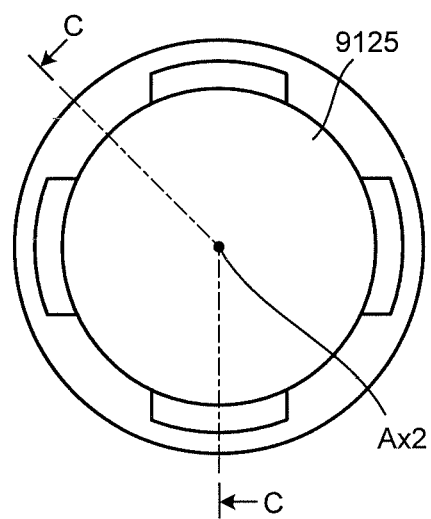
FIG. 14 is a plan view illustrating the configuration of the main portion of the air/water supply button and is a view for explaining the configuration of the shaft portion.
Figure 15:
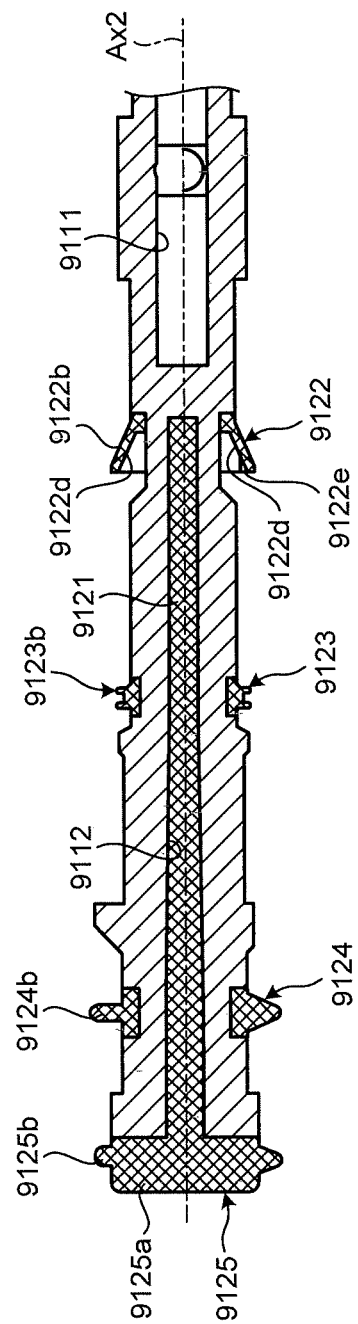
FIG. 15 is a cross-sectional view taken along line C-C illustrated in FIG. 14.

FIG. 8 is a view for explaining a configuration of a main portion of the air/water supply button 9 and is a perspective view illustrating a configuration of the shaft portion 91. FIG. 9 is a view for explaining the configuration of the main portion of the air/water supply button 9, and is a partially cross-sectional view illustrating the configuration of the shaft portion 91. FIG. 10 is a cross-sectional view taken along line A-A illustrated in FIG. 9. FIG. 11 is a cross-sectional view taken along line B-B illustrated in FIG. 9. FIG. 12 is an enlarged view of a region $R_1$ illustrated in FIG. 9. FIG. 13 is an enlarged view of a region $R_2$ illustrated in FIG. 9. FIG. 14 is a plan view illustrating the configuration of the main portion of the air/water supply button 9 and is a view for explaining the configuration of the shaft portion 91. FIG. 15 is a cross-sectional view taken along line C-C illustrated in FIG. 14.

The shaft portion 91 has a main body portion 911 and a seal member 912. As illustrated in FIG. 9, the main body portion 911 extends in a substantially rod shape. Further, the main body portion 911 includes a first hole portion 9111 which forms a hollow space extending in a central axis Ax2 direction and a second hole portion 9112 which forms a hollow space extending in the central axis direction, the hollow space being independent of the hollow space formed by the first hole portion 9111.

As illustrated in FIGS. 8 and 9, the first hole portion 9111 extends from one end of the central axis Ax2 of the shaft portion 91, and the other end is located in the main body portion 911. The central axis Ax2 passes through the first hole portion 9111. Further, the main body portion 911 includes a communication hole 9111a which communicates with a side surface in a direction orthogonal to the central axis Ax2 and the first hole portion 9111.

The second hole portion 9112 extends from the other end of the central axis Ax2 of the shaft portion 91 and one end of the second hole portion 9112 is located in the main body portion 911. The central axis Ax2 passes through the second hole portion 9112. Further, the main body portion 911 includes communication holes 9112a to 9112c which communicate with a side surface in the direction orthogonal to the central axis Ax2 and the second hole portion 9112.

The seal member 912 has a support portion 9121 and protrusion portions 9122 to 9125. The seal member 912 is formed by integrally molding the support portion 9121 and the protrusion portions 9122 to 9125. The support portion 9121 is disposed in the second hole portion 9112 and supports each of the protrusion portions 9122 to 9125. The seal member 912 is formed using an elastic member such as rubber or a resin.

The protrusion portion 9122 has a branch portion 9122a connected to the support portion 9121 and an exposed portion 9122b provided on an end portion of the branch portion 9122a on a side opposite to a side connected to the support portion 9121. The branch portion 9122a is disposed in the communication hole 9112a. At least a portion of the exposed portion 9122b protrudes from an outer surface of the main body portion 911 via the communication hole 9112a.

The exposed portion 9122b goes around the outer surface of the main body portion 911. Specifically, as illustrated in FIGS. 9 and 12, the exposed portion 9122b has a conical shape of which diameter of an outer periphery increases along the central axis Ax2 direction. The exposed portion 9122b has a thick portion 9122c having a large thickness in the central axis Ax2 direction and a thin portion 9122d of which thickness in the central axis Ax2 direction is thinner than that of the thick portion 9122c. In addition, as illustrated in FIGS. 11 and 15, a wide portion 9122e in which a width of an end portion increases in order to increase strength of the thin portion 9122d is formed in the thin portion 9122d. In the exposed portion 9122b, at least the thin portion 9122d is deformed by a change in an air pressure. Therefore, the protrusion portion 9122 functions as a check valve in the air/water supply button 9. Hereinafter, the protrusion portion 9122 may be referred to as a check valve 9122.

The protrusion portion 9123 has a branch portion 9123a connected to the support portion 9121 and an exposed portion 9123b provided on an end portion of the branch portion 9123a on a side opposite to a side connected to the support portion 9121. The branch portion 9123a is disposed in the communication hole 9112b. The exposed portion 9123b protrudes at least partially from the outer surface of the main body portion 911 through the communication hole 9112b.

The exposed portion 9123b goes around the outer surface of the main body portion 911. Specifically, as illustrated in FIG. 13, the exposed portion 9123b has two protrusions (protrusions 9123c and 9123d) which protrude from the outer surface of the main body portion 911. In the following description, the protrusions 9123c and 9123d are described as having the same shape, but may be formed in different shapes as long as a function is not impaired.

In the exposed portion 9123b, when a length of each of the protrusions 9123c and 9123d in a direction orthogonal to the central axis Ax2 is indicated by $d_1$, a maximum length of the protrusion 9123c in the central axis Ax2 direction is indicated by $d_2$, a distance between the protrusions 9123c and 9123d which is a distance (pitch) between end portions in the central axis Ax2 direction is indicated by $d_3$, and a shrinkage amount of the protrusion 9123c when the protrusion 9123c comes into press-contact with a pressure-contact object is indicated by $d_4$, relationships of $d_2 \leq d_1$, $2d_2 \leq d_3$, and $d_4 < d_1$ are satisfied. By setting the protrusions 9123c and 9123d to satisfy this relationship, the protrusions 9123c and 9123d are deformed so as to fall down when a contact position is changed in a state where the protrusions 9123c and 9123d are in contact with the abutment object. In this manner, the protrusions 9123c and 9123d are deformed so as to fall down, and an amount of operating force generated between the protrusions 9123c and 9123d and the abutment object when the contact position is changed may be small compared to a case where the protrusion is deformed while being crushed.

The protrusion portion 9124 has a branch portion 9124a connected to the support portion 9121 and an exposed portion 9124b provided on an end portion of the branch portion 9124a on a side opposite to a side connected to the support portion 9121. The branch portion 9124a is disposed in the communication hole 9112c. At least a portion of the exposed portion 9124b protrudes from the outer surface of the main body portion 911 via the communication hole 9112c and the exposed portion 9124b goes around the outer surface of the main body portion 911.

The protrusion portion 9125 is provided on an end portion of the main body portion 911 and has a base 9125a connected to the support portion 9121 and an exposed portion 9125b provided on an end portion of the base 9125a on a side opposite to a side connected to the support portion 9121. The base 9125a is a portion corresponding to the above-described branch portions 9122a to 9124a described above, and extends outside the first hole portion 9111. The exposed portion 9125b protrudes from the base 9125a in a direction orthogonal to the central axis Ax2. The exposed portion 9125b is exposed to the outside of a virtual region in which a cross section of the portion having a largest diameter of the main body portion 911 extends along the central axis Ax2.

In the shaft portion 91, the exposed portions 9122b to 9125b of the seal member 912 are supported by the support portion 9121 provided inside the main body portion 911. Accordingly, in the shaft portion 91, a cross-sectional secondary moment decreases compared to a configuration in which only the seal member goes around the outer surface of the main body portion 911. Thereby, for example, even when a load in the central axis Ax2 direction is applied to each of the exposed portion 9122b to 9125b, peeling of each of the exposed portion 9122b to 9125b from the main body portion 911 may be suppressed.

Figure 16:
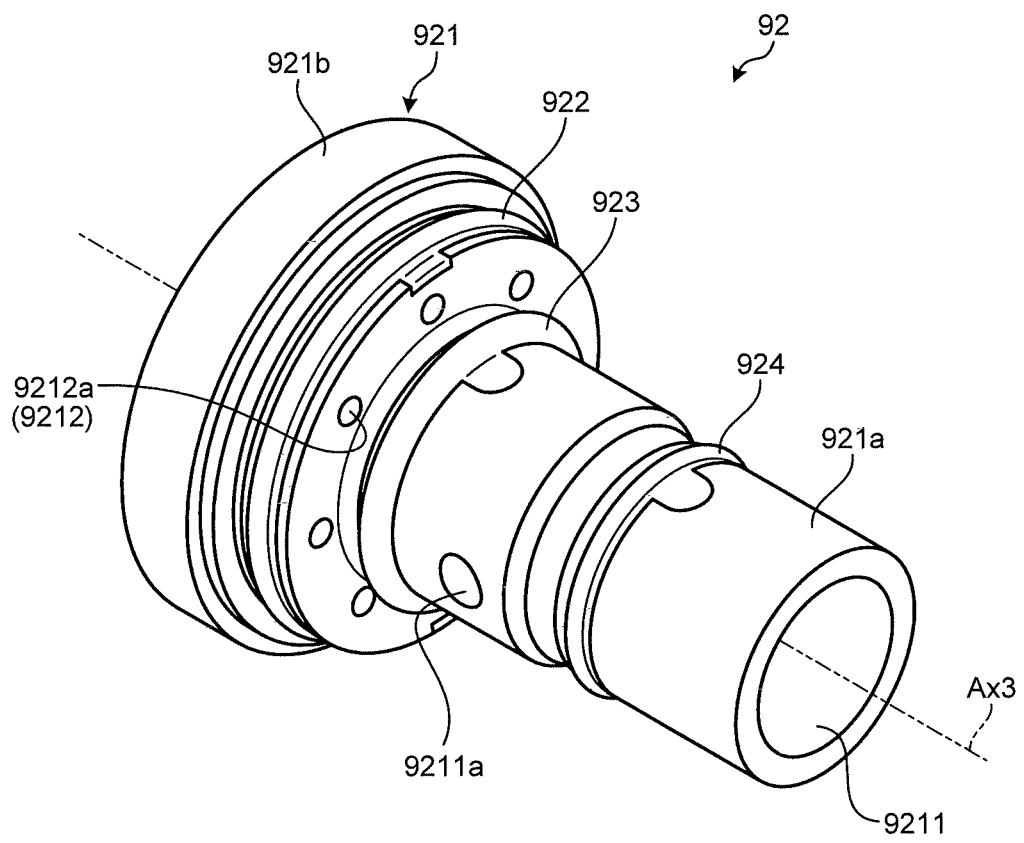
FIG. 16 is a view for explaining the configuration of the main portion of the air/water supply button, and is a perspective view illustrating a configuration of a first member.
Figure 17:
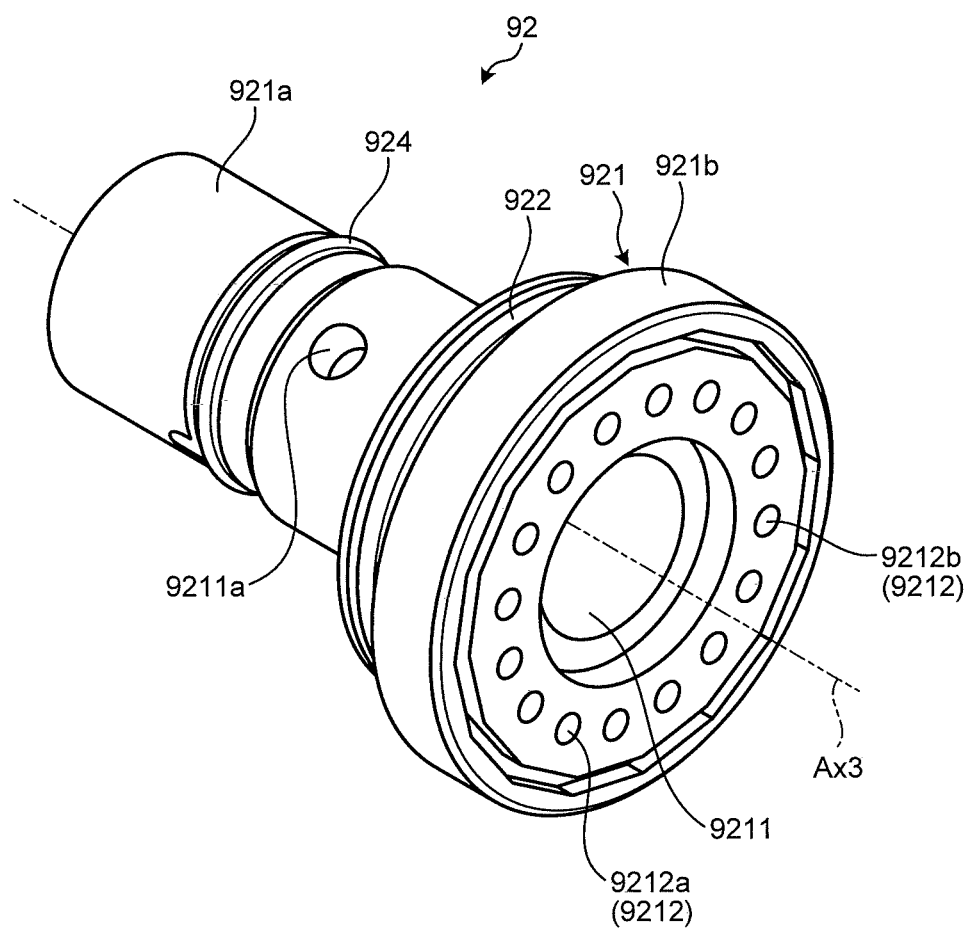
FIG. 17 is a view for explaining the configuration of the main portion of the air/water supply button, and is a perspective view illustrating the configuration of the first member.
Figure 18:
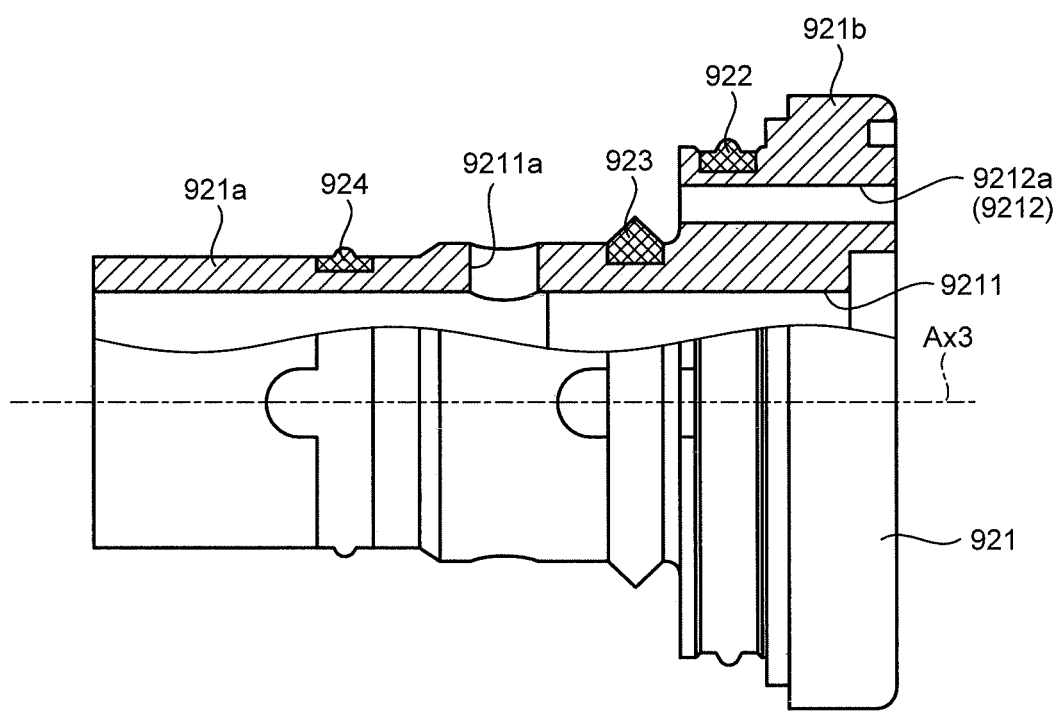
FIG. 18 is a view for explaining the configuration of the main portion of the air/water supply button, and is a partially cross-sectional view illustrating the configuration of the first member.

FIGS. 16 and 17 are views for explaining the configuration of the main portion of the air/water supply button 9 and perspective views illustrating the configuration of the first member 92. FIG. 18 is a view for explaining the configuration of the main portion of the air/water supply button 9, and is a partially cross-sectional view illustrating the configuration of the first member 92. FIGS. 16 to 18 are views for explaining the configuration of the first member 92. FIG. 17 is a view when the first member 92 illustrated in FIG. 16 viewed from an opposite side in a central axis Ax3 direction. FIG. 18 is a partially cross-sectional view in which a plane passing through the central axis Ax3 is a cut surface.

The first member 92 includes a main body portion 921 which forms a hollow space 9211 extending along the central axis Ax3, and seal members 922 to 924 which go around the outer surface of the main body portion 921 and protrude from the outer surface of the main body portion 921, respectively.

The main body portion 921 has a first cylindrical portion 921a extending in a cylindrical shape and a second cylindrical portion 921b which is connected to the first cylindrical portion 921a and extends in a cylindrical shape of which diameter forming an outer periphery is larger than a diameter of the first cylindrical portion 921a.
The seal member 922 is provided on an outer periphery of the second cylindrical portion 921b. The seal members 923 and 924 are provided on an outer periphery of the first cylindrical portion 921a. A communication hole 9211a which communicates an outer surface of the main body portion 921 and the hollow space 9211 is formed in the main body portion 921. The communication hole 9211a has an aperture between the seal member 923 and the seal member 924 and forms a hollow space extending in a direction orthogonal to the central axis Ax3.

Moreover, a plurality of holes 9212 which are formed in the second cylindrical portion 921b and extend in the central axis Ax3 direction are provided in the main body portion 921. The hole 9212 includes communication holes 9212a which penetrate in the central axis Ax3 direction and communicate with one surface and the other surface of the second cylindrical portion 921b in the central axis Ax3 direction and bottomed cylindrical concave portions 9212b which extend in the central axis Ax3 direction from the one surface in the central axis Ax3 direction. As illustrated in FIG. 17, the communication holes 9212a and the concave portions 9212b are alternately arranged so as to go around the central axis Ax3.

Figure 19:
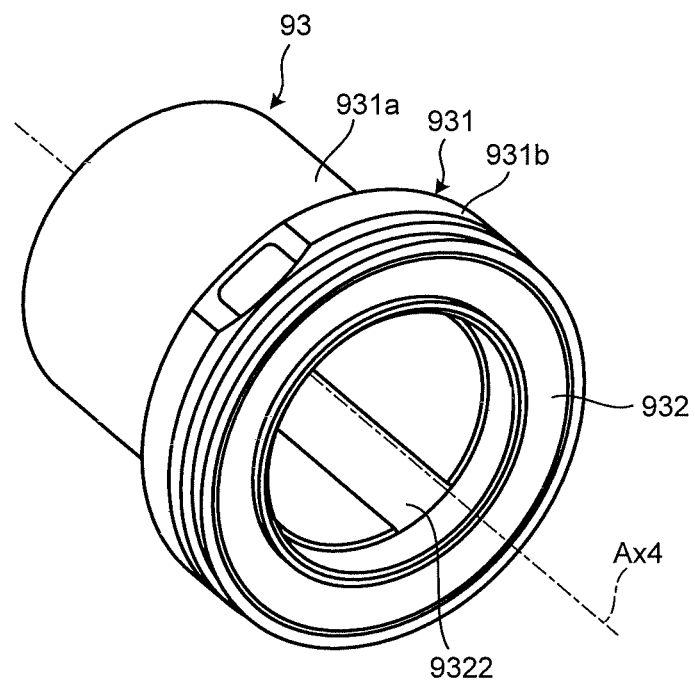
FIG. 19 is a view for explaining the configuration of the main portion of the air/water supply button, and is a perspective view illustrating a configuration of a second member.
Figure 20:
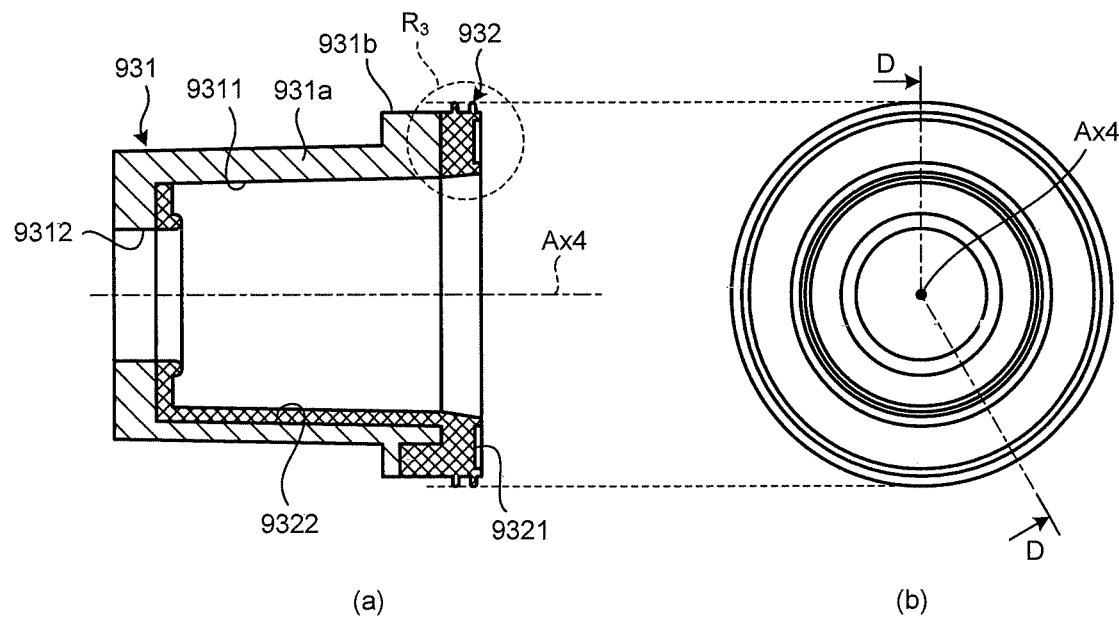
FIG. 20 is a view for explaining the configuration of the main portion of the air/water supply button, and is a view illustrating the configuration of the second member.
Figure 21:
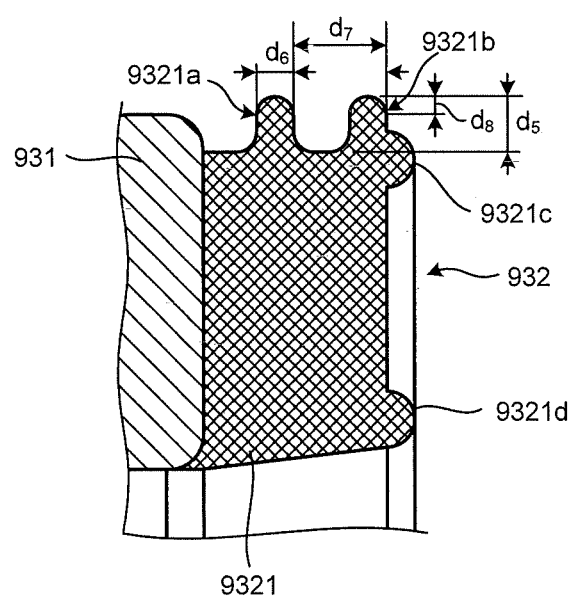
FIG. 21 is an enlarged view of a region $R_3$ illustrated in (a) of FIG. 20.

FIG. 19 is a view for explaining the configuration of the main portion of the air/water supply button 9, and is a perspective view illustrating a configuration of the second member 93. FIG. 20 is a view for explaining the configuration of the main portion of the air/water supply button 9, and is a view illustrating the configuration of the second member 93. (a) of FIG. 20 is a cross-sectional view in which a plane which is parallel to a central axis Ax4 and passes through the central axis Ax4 is a cut surface, and (b) of FIG. 20 is a plan view when viewed in the central axis Ax4 direction. Specifically, (a) of FIG. 20 is a cross-sectional view taken along line D-D illustrated in (b) of FIG. 20. FIG. 21 is an enlarged view of a region $R_3$ illustrated in (a) of FIG. 20. FIGS. 19 to 21 are views for explaining the configuration of the second member 93.

The second member 93 has a main body portion 931 which forms a hollow space extending along the central axis Ax4 and a seal member 932 provided on one end of the main body portion 931 in the central axis Ax4 direction.

The main body portion 931 has a first cylindrical portion 931a extending in a cylindrical shape, and a second cylindrical portion 931b which is connected to the first cylindrical portion 931a and extends in a cylindrical shape of which diameter forming an outer periphery is larger than a diameter of the first cylindrical portion 931a. Moreover, in the main body portion 931, a first hole portion 9311 which forms a hollow space extending in the central axis Ax4 direction from the end portion on the second cylindrical portion 931b side, and a second hole portion 9312 which is connected to the hollow space formed by the first hole portion 9311 and forms a hollow space smaller than the hollow space formed by the first hole portion 9311. In the main body portion 931, a hollow space having a stepped shape along the central axis Ax4 is formed by a wall surface of the first hole portion 9311 and a wall surface of the second hole portion 9312.

The seal member 932 is formed using an elastic member such as rubber or a resin. The seal member 932 has an annular seal portion 9321 which is an end portion of the second cylindrical portion 931b and provided on a surface orthogonal to the central axis Ax4 and an extension portion 9322 which is connected to a portion of the seal portion 9321 and extends along a wall surface of the first hole portion 9311.

The seal portion 9321 has a hollow disk shape with the central axis Ax4 as a symmetry axis. Specifically, as illustrated in FIGS. 19 and 20, the seal portion 9321 has an annular shape as viewed from the central axis Ax4 direction. As illustrated in FIG. 21, the seal portion 9321 has two first protrusions (first protrusions 9321a and 9321b) protruding in a direction orthogonal to the central axis Ax4 and two second protrusions (second protrusions 9321c and 9321d) protruding along the central axis Ax4 direction. In the following descriptions, the first protrusions 9321a and 9321b and the second protrusions 9321c and 9321d are described as having the same shape as each other, but they may have different shapes as long as functions thereof are not impaired.

In the seal portion 9321, when a length of each of the first protrusions 9321a and 9321b in the direction orthogonal to the central axis Ax4 is indicated by $d_5$, a maximum length of the first protrusion 9321a in the central axis Ax4 direction is indicated by $d_6$, a distance between the first protrusion 9321a and the first protrusion 9321b which is a distance (pitch) between end portions in the central axis Ax4 direction is indicated by $d_7$, and a shrinkage amount of each of the first protrusions 9321a and 9321b when the first protrusions 9321a and 9321b come into pressure-contact with a pressure-contact object is indicated by $d_8$, relationships of $d_6 \leq d_5$, $2d_6 \leq d_7$, and $d_8 < d_5$ are satisfied. By setting the first protrusions 9321a and 9321b to satisfy this relationship, the first protrusions 9321a and 9321b are deformed so as to fall down when a contact position is changed in a state where the first protrusions 9321a and 9321b are in contact with the abutment object. In this manner, the first protrusions 9321a and 9321b are deformed so as to fall down, and an amount of operating force generated between the first protrusions 9321a and 9321b and the abutment object when the contact position is changed may be small compared to a case where the protrusion is deformed while being crushed.

Figure 22:
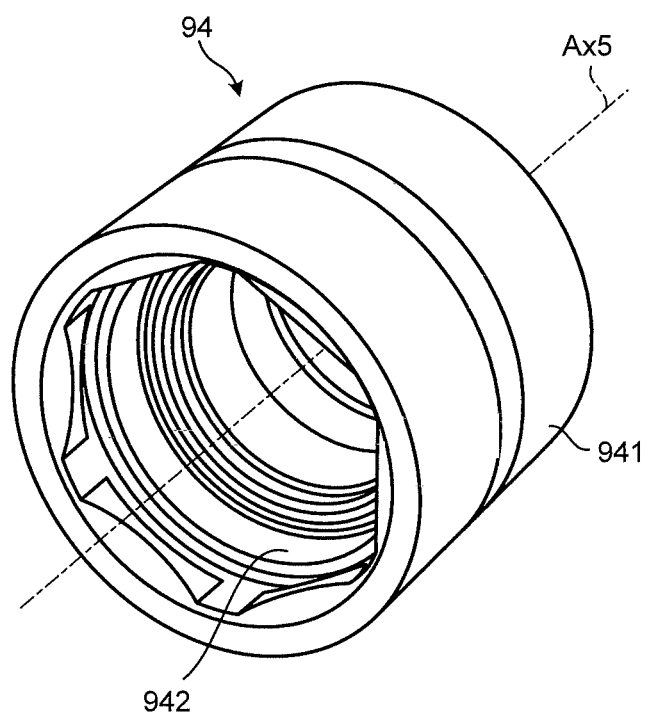
FIG. 22 is a view for explaining the configuration of the main portion of the air/water supply button, and is a perspective view illustrating a configuration of an attachment member.
Figure 23:
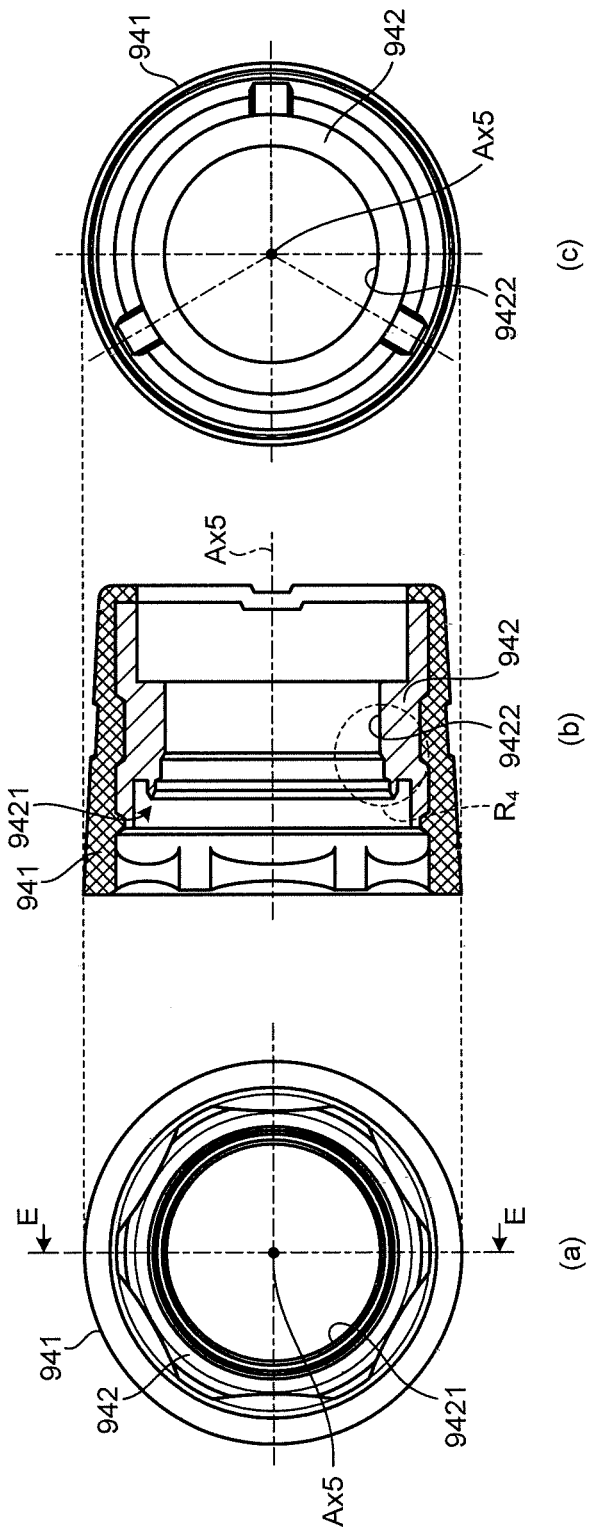
FIG. 23 is a view for explaining the configuration of the main portion of the air/water supply button, and is a view illustrating the configuration of the attachment member.

FIG. 22 is a view for explaining the configuration of the main portion of the air/water supply button 9, and is a perspective view illustrating a configuration of an attachment member 94. FIG. 23 is a view for explaining the configuration of the main portion of the air/water supply button 9, and is a view illustrating the configuration of the attachment member 94. FIGS. 22 and 23 are view for explaining the configuration of the attachment member 94. (a) of FIG. 23 is a plan view when viewed from one end side in a central axis Ax5 direction, (b) of FIG. 23 is a cross-sectional view taken along line E-E of (a) of FIG. 23, and (c) of FIG. 23 is a plan view when the attachment member 94 illustrated in (a) of FIG. 23 is viewed from an opposite side in the central axis Ax5.

The attachment member 94 has a tubular first member 941 forming a hollow space extending along the central axis Ax5, and a tubular second member 942 provided inside the first member 941. The first member 941 is locked to the first cylinder 7, and thus, the attachment member 94 is attached to the ultrasound endoscope 2.

The second member 942 is provided on one end in the central axis Ax5 direction and has a connection portion 9421 connected to the first member 941. In addition, in the second member 942, an inner peripheral surface 9422 of which at least a portion may come into contact with the first protrusions 9321a and 9321b of the seal portion 9321 is formed.

Figure 24:
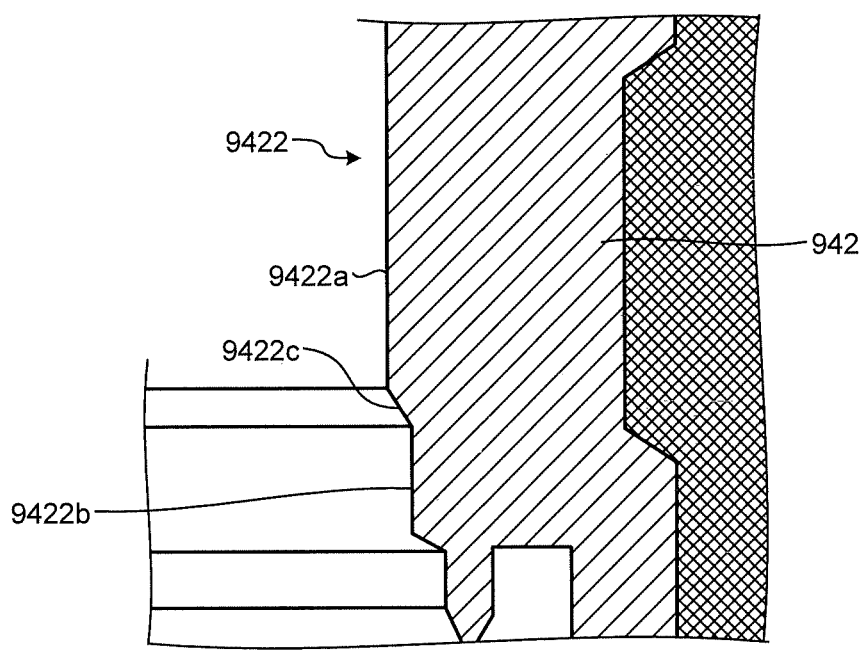
FIG. 24 is an enlarged view of a region $R_4$ illustrated in (b) of FIG. 23.

FIG. 24 is an enlarged view of a region $R_4$ illustrated in (b) of FIG. 23. The inner peripheral surface 9422 includes a first inner peripheral surface 9422a which goes around the central axis Ax5 as a center axis, a second inner peripheral surface 9422b which goes around the center axis Ax5 as a center axis and of which diameter in a direction orthogonal to the central axis Ax5 is larger than a diameter forming the first inner peripheral surface 9422a, and an inclination surface 9422c which is inclined to the central axis Ax5, goes around the central axis Ax5 as the central axis, and connects the first inner peripheral surface 9422a and the second inner peripheral surface 9422b to each other. Each of the first inner peripheral surface 9422a, the second inner peripheral surface 9422b, and the inclination surface 9422c is axially symmetric with respect to the central axis Ax5.

The diameter of the first inner peripheral surface 9422a is slightly smaller than the diameter of the distal end of each of the first protrusions 9321a and 9321b. Specifically, the diameter of the first inner peripheral surface 9422a is a diameter obtained by reducing the diameter of the distal end of each of the first protrusions 9321a and 9321b based on the above-described shrinkage amount $d_8$.

The diameter of the second inner peripheral surface 9422b is the same as or slightly larger than the diameter of the distal end of each of the first protrusions 9321a and 9321b. Specifically, the diameter of the second inner peripheral surface 9422b is equal to or more than the diameter of the distal end of each of the first protrusions 9321a and 9321b, and the attachment member 94 is smaller than the diameter of the outer periphery of the main body portion 921 of the first member 92.

In the ultrasound endoscope 2, according to a push-in amount of the air/water supply button 9 with respect to the first cylinder 7, a first flow path through which a gas discharged from the distal end of the insertion portion 21 flows, a second flow path through which a liquid discharged from the distal end of the insertion portion 21 flows, and a third flow path which leads to the inside of the balloon attached to the distal end of the insertion portion 21 are switched in this order. In the first inner peripheral surface 9422a, the second inner peripheral surface 9422b, and the inclination surface 9422c, the first inner peripheral surface 9422a is provided according to a position of the seal portion 9321 which forms the first flow path, and the inclination surface 9422c and the second inner peripheral surface 9422b are provided according to the position of the seal portion 9321 which is switched between the first flow path and the second flow path.

Figure 25A:
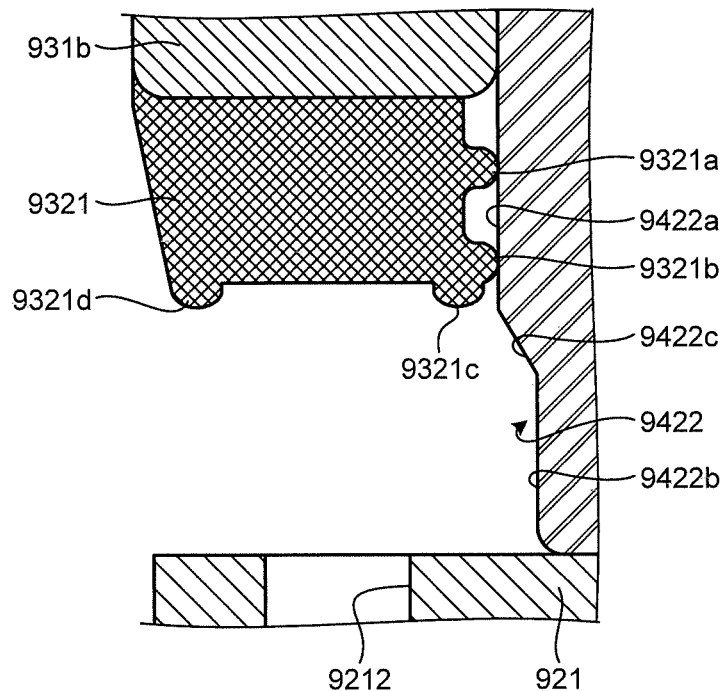
FIG. 25A is a view for explaining the configuration of the main portion of the air/water supply button, and a view for explaining a contact state (part 1) when the second member moves with respect to the attachment member.
Figure 25B:
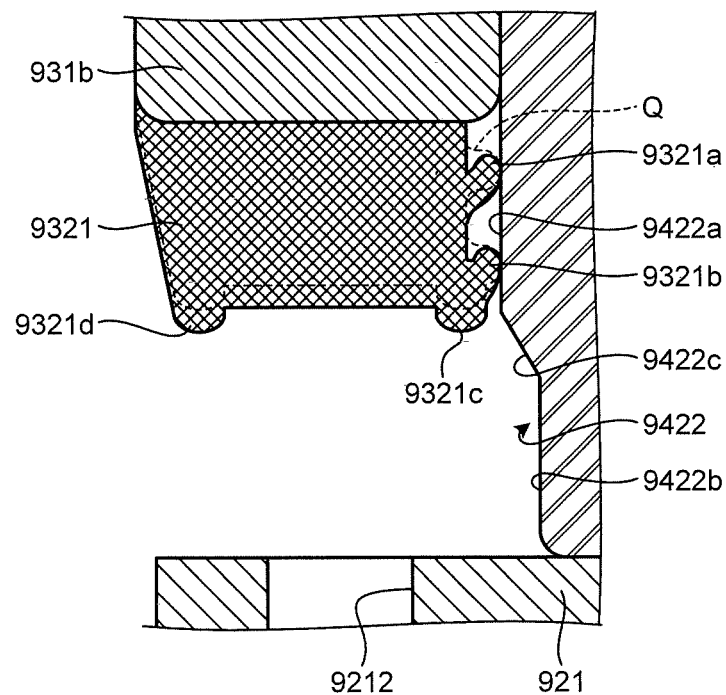
FIG. 25B is a view for explaining the configuration of the main portion of the air/water supply button, and a view for explaining the contact state (part 2) when the second member moves with respect to the attachment member.
Figure 25C:
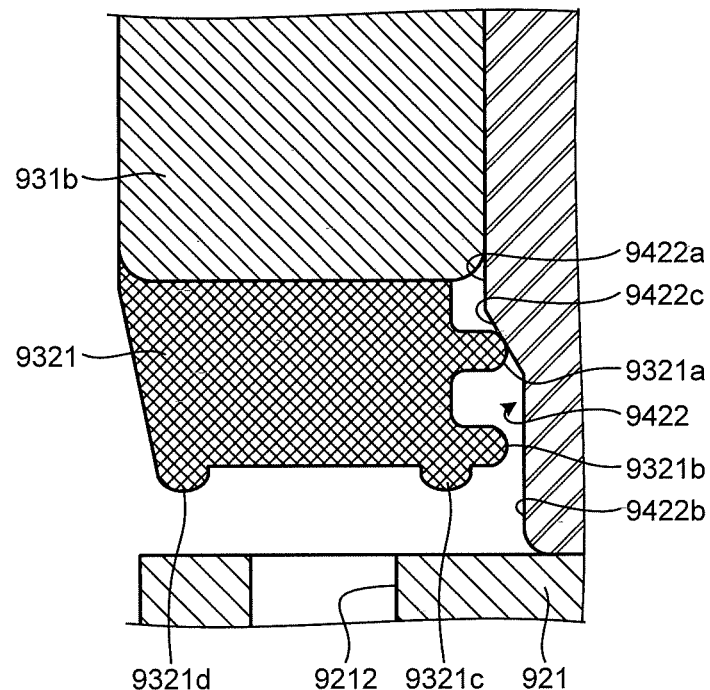
FIG. 25C is a view for explaining the configuration of the main portion of the air/water supply button, and a view for explaining the contact state (part 3) when the second member moves with respect to the attachment member.
Figure 25D:
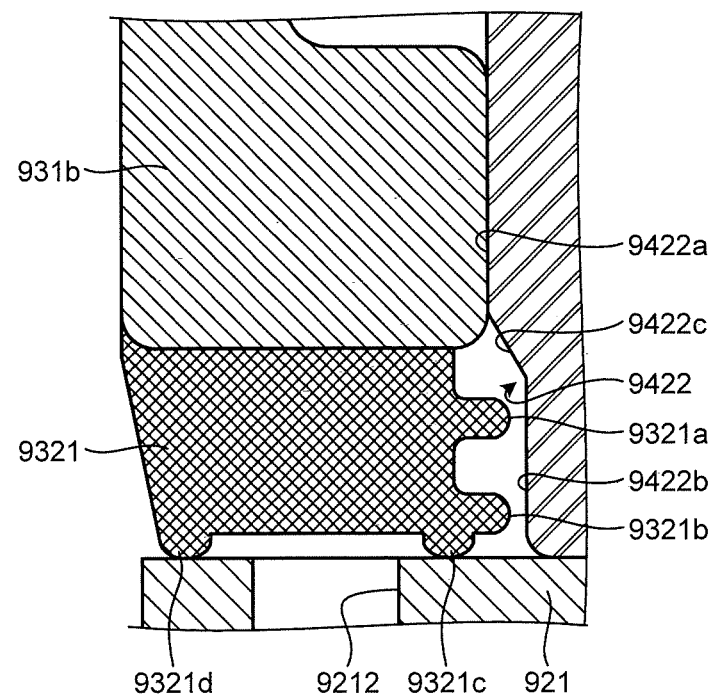
FIG. 25D is a view for explaining the configuration of the main portion of the air/water supply button, and a view for explaining the contact state (part 4) when the second member moves with respect to the attachment member.
Figure 25E:
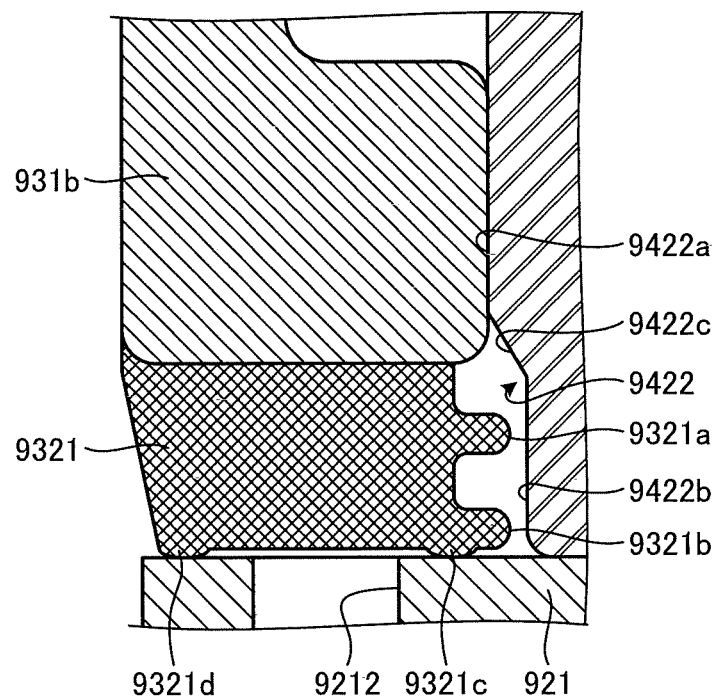
FIG. 25E is a view for explaining the configuration of the main portion of the air/water supply button, and a view for explaining the contact state (part 5) when the second member moves with respect to the attachment member.

Here, a contact mode between the second member 93 and the attachment member 94 when the air/water supply button 9 is pushed into the first cylinder 7 will be described with reference to FIGS. 25A to 25E. FIG. 25A is a view for explaining the configuration of the main portion of the air/water supply button 9, and a view for explaining a contact state (part 1) when the second member 93 moves with respect to the attachment member 94. FIG. 25B is a view for explaining the configuration of the main portion of the air/water supply button 9, and a view for explaining the contact state (part 2) when the second member 93 moves with respect to the attachment member 94. FIG. 25C is a view for explaining the configuration of the main portion of the air/water supply button 9, and a view for explaining the contact state (part 3) when the second member 93 moves with respect to the attachment member 94. FIG. 25D is a view for explaining the configuration of the main portion of the air/water supply button 9, and a view for explaining the contact state (part 4) when the second member 93 moves with respect to the attachment member 94. FIG. 25E is a view for explaining the configuration of the main portion of the air/water supply button 9, and a view for explaining the contact state (part 5) when the second member 93 moves with respect to the attachment member 94. The seal portion 9321 abuts the inner peripheral surface 9422 of the attachment member 94, which is a surface forming a hollow space extending in the central axis Ax5 direction of the attachment member 94.

First, in a case where the air/water supply button 9 is not operated at all, as illustrated in FIG. 25A, the first protrusions 9321a and 9321b are in pressure contact with the first inner peripheral surface 9422a, and thus, a portion between the second member 93 and the attachment member 94 is airtightly or watertightly sealed.

Thereafter, if the air/water supply button 9 is pushed into the first cylinder 7 by a user and the second member 93 moves downward in FIG. 25B which is the central axis direction, the first protrusions 9321a and 9321b are deformed to fall on a side opposite to a forward movement direction of the second member 93. In other words, each of the first protrusions 9321a and 9321b rotate with a proximal end in a protrusion direction as a supporting point. In addition, broken lines Q illustrated in FIG. 25B indicate a position of the seal portion 9321 in FIG. 25A. In addition, depending on how the air/water supply button 9 is attached to the first cylinder 7, the first protrusions 9321a and 9321b may already be in the fallen state in the state (FIG. 25A) where no operation is performed.

If the air/water supply button 9 is further pushed into the first cylinder 7, the first protrusions 9321a and 9321b slide on the inclination surface 9422c (refer to FIG. 25C). After the first protrusions 9321a and 9321b slide on the inclination surface 9422c, the first protrusions 9321a and 9321b reach the second inner peripheral surface 9422b from the inclination surface 9422c or immediately before the contact surfaces shift from the inclination surface 9422c to the second inner peripheral surface 9422b, the first protrusions 9321a and 9321b are released from the inner peripheral surface 9422 and are in a non-contact state (refer to FIG. 25D). At this time, immediately before the first protrusions 9321a and 9321b are released from the inner peripheral surface 9422, or simultaneously with the release of the first protrusions 9321a and 9321b from the inner peripheral surface 9422, the second protrusions 9321c and 9321d abut the first member 92, and an aperture of the hole 9212 is closed. Accordingly, the hole 9212 is sealed by the seal portion 9321 and a fluid communication between the air/water supply button 9 and the communication passage 721 is interrupted.

As illustrated in FIG. 25E, if the air/water supply button 9 is further pushed into the first cylinder 7, a pressure contact of each of the second protrusions 9321c and 9321d to the main body portion 921 of the first member 92 becomes stronger, and thus, air tightness or water tightness may be further ensured.

Figure 26:
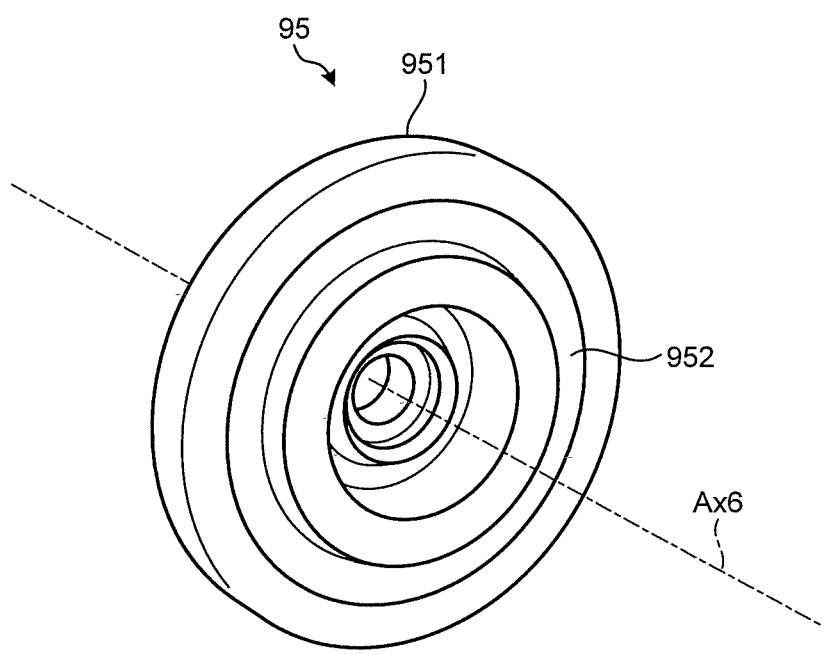
FIG. 26 is a view for explaining the configuration of the main portion of the air/water supply button, and is a perspective view illustrating a configuration of a cap.
Figure 27:
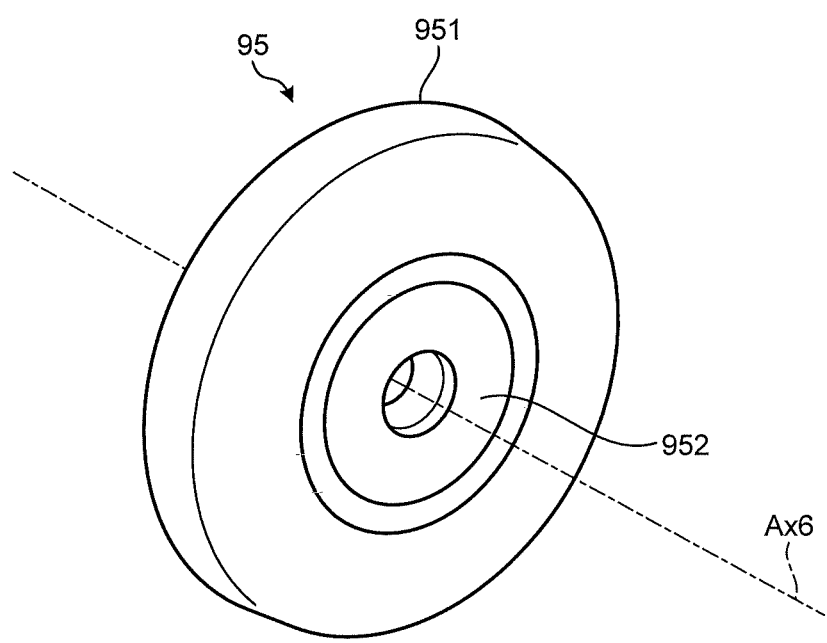
FIG. 27 is a view for explaining the configuration of the main portion of the air/water supply button, and is a perspective view illustrating the configuration of the cap.
Figure 28:
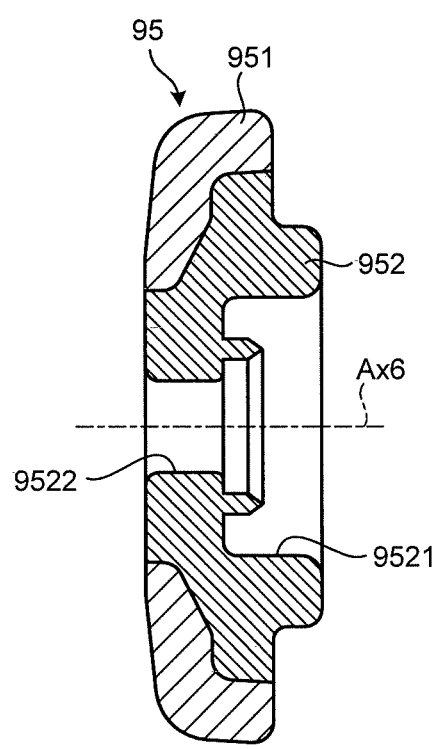
FIG. 28 is a view for explaining the configuration of the main portion of the air/water supply button, and is a cross-sectional view illustrating the configuration of the cap.
Figure 29:
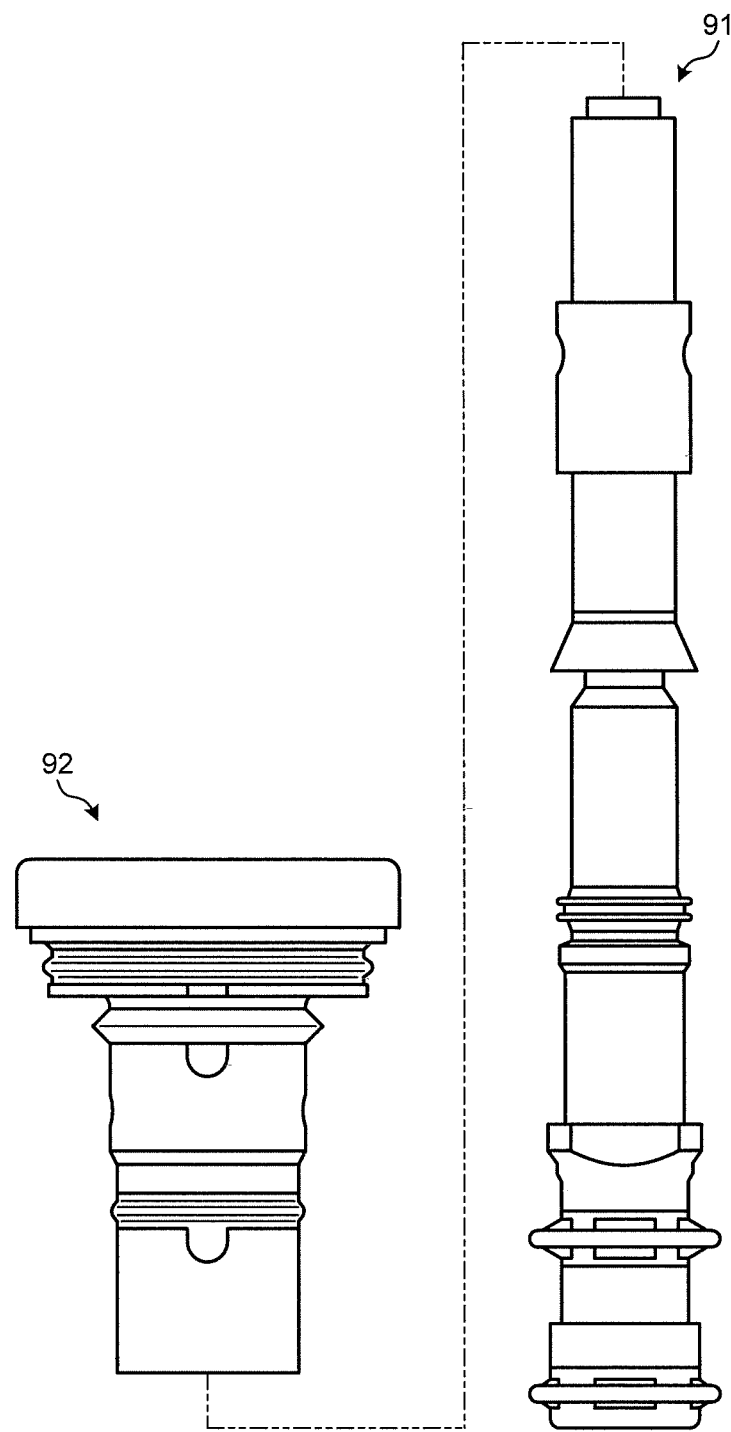
FIG. 29 is a view for explaining assembly (part 1) of the air/water supply button.

FIGS. 26 and 27 are views for explaining the configuration of the main portion of the air/water supply button 9, and are perspective views illustrating a configuration of the cap 95. FIG. 28 is a view for explaining the configuration of the main portion of the air/water supply button 9, and is a cross-sectional view illustrating the configuration of the cap 95. FIGS. 26 to 28 are views for explaining the configuration of the cap 95. FIG. 27 is a view when the cap 95 illustrated in FIG. 26 is viewed from an opposite side in a central axis Ax6 direction. FIG. 28 is a cross-sectional view in which a plane which is parallel to the central axis Ax6 and passes through the central axis Ax6 is a cut surface.

The cap 95 has a hollow disk-shaped first member 951 and a second member 952 provided inside the first member 951.

In the second member 952, a first hole portion 9521 which is notched from one end side in the central axis Ax6 direction and to which one end of the shaft portion 91 is attached, and a second hole portion 9522 which is connected to the first hole portion 9521 and forms a hollow space extending to the other end in the central axis Ax6 direction are formed. The second hole portion 9522 is a portion through which gas in the air/water supply button 9 leaks, and hereinafter, may be referred to as a leak hole 9522.

The first coil spring 96 is formed by spirally winding a wire. The first coil spring 96 is provided between the first member 92 and the second member 93, and applies a biasing force in a direction away from each other to the first member 92 and the second member 93. The first coil spring 96 corresponds to a first elastic body, and biases the second member 93 such that the second member 93 moves to a side which is one end side of the shaft portion 91 and is connected to the cap 95.

The second coil spring 97 is formed by spirally winding a wire. The second coil spring 97 is provided between the second member 93 and the cap 95 and applies a biasing force in a direction away from each other to the second member 93 and the cap 95. A diameter of the wire of second coil spring 97 is larger than a diameter of the wire of first coil spring 96. In addition, the diameter of the wire of the second coil spring 97 may be equal to or smaller than the diameter of the wire of the first coil spring 96 as long as a spring constant of the second coil spring 97 is larger than a spring constant of the first coil spring 96.

Next, assembly of the air/water supply button 9 will be described with reference to FIGS. 29 to 40. FIGS. 29 to 40 illustrate the assembly of the air/water supply button 9. First, the first member 92 is attached to the shaft portion 91. In this case, the shaft portion 91 (main body portion 911) is inserted into the first member 92 (refer to FIGS. 29 and 30). As a result, a structure 100A in which the first member 92 is supported by the shaft portion 91 is obtained.

Figure 30:
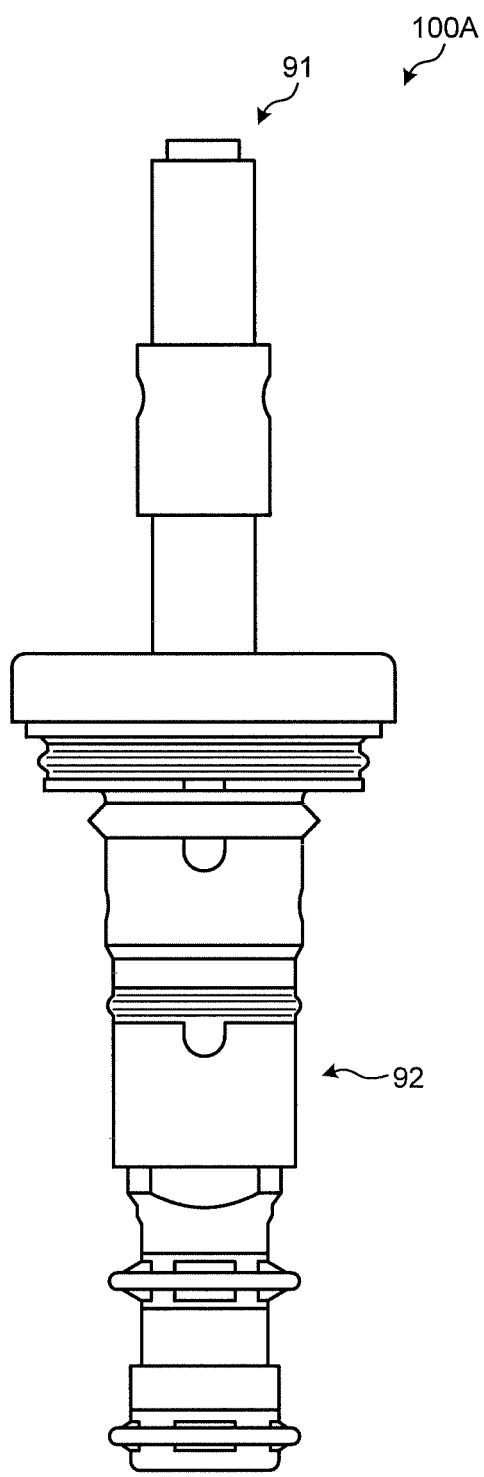
FIG. 30 is a view for explaining the assembly (part 1) of the air/water supply button.
Figure 31:
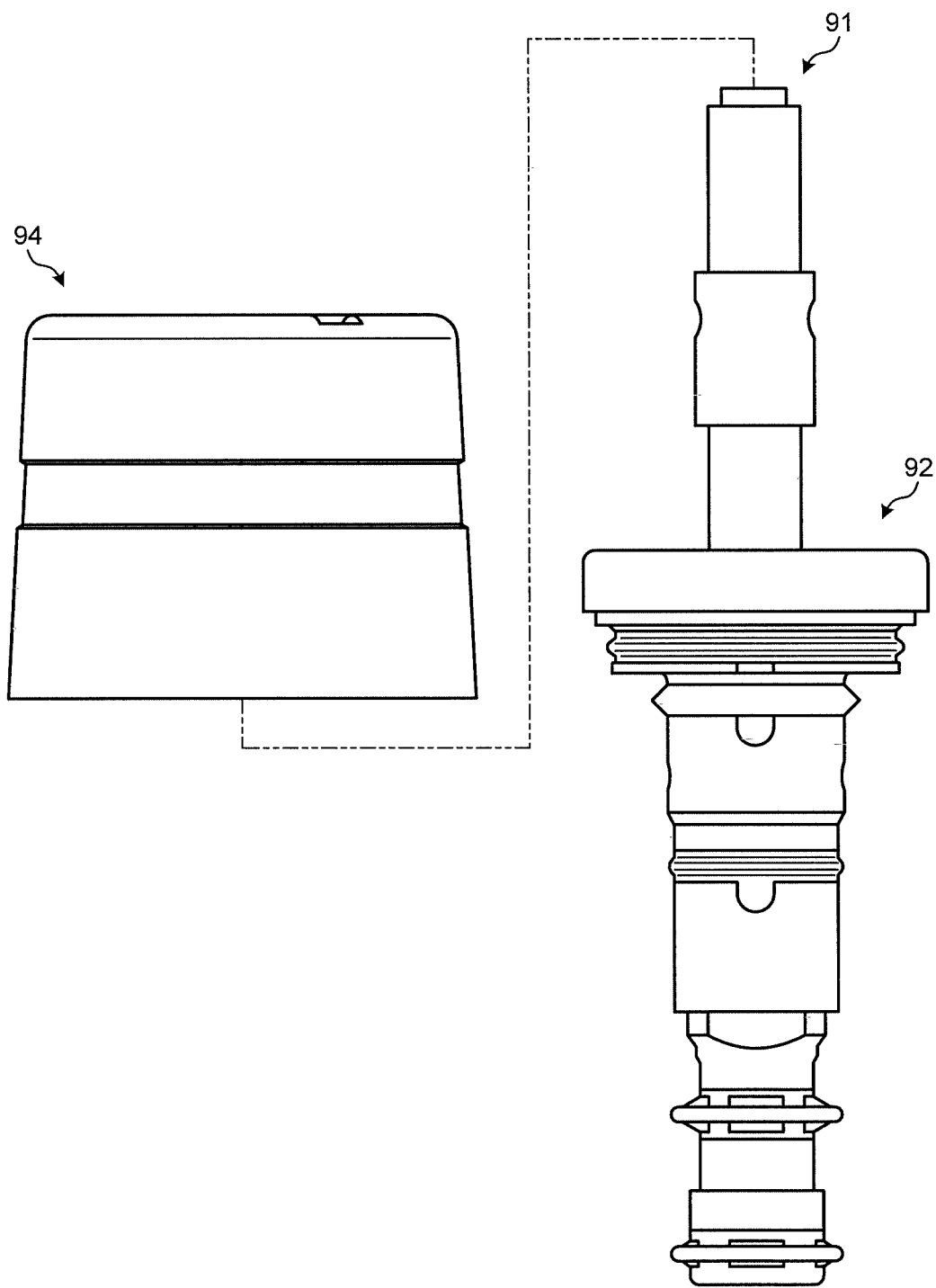
FIG. 31 is a view for explaining the assembly (part 2) of the air/water supply button.

After the structure 100A illustrated in FIG. 30 is obtained, the attachment member 94 is attached to the shaft portion 91 (refer to FIG. 31). In this case, the first member 92 and the attachment member 94 are fixed to each other by ultrasonic welding. Accordingly, a structure 100B in which the attachment member 94 is supported by the first member 92 is obtained (refer to FIG. 32).

Figure 32:
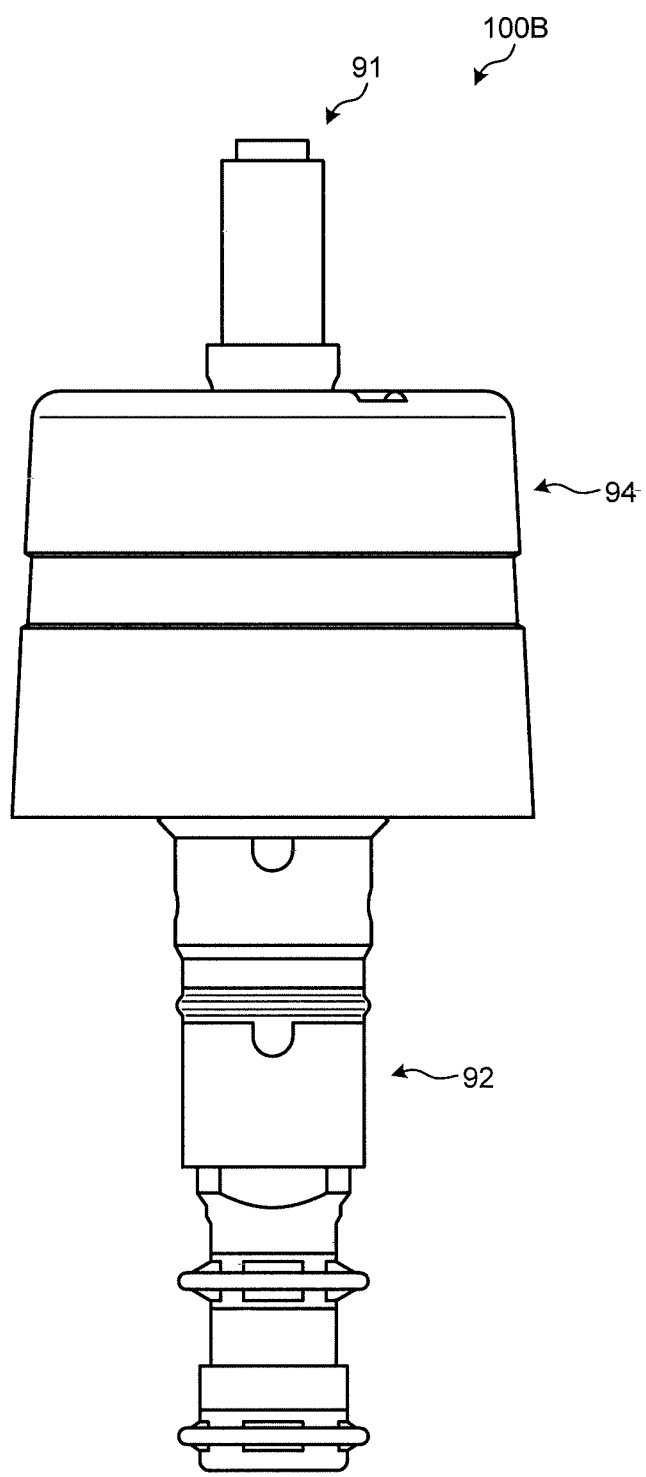
FIG. 32 is a view for explaining the assembly (part 2) of the air/water supply button.
Figure 33:
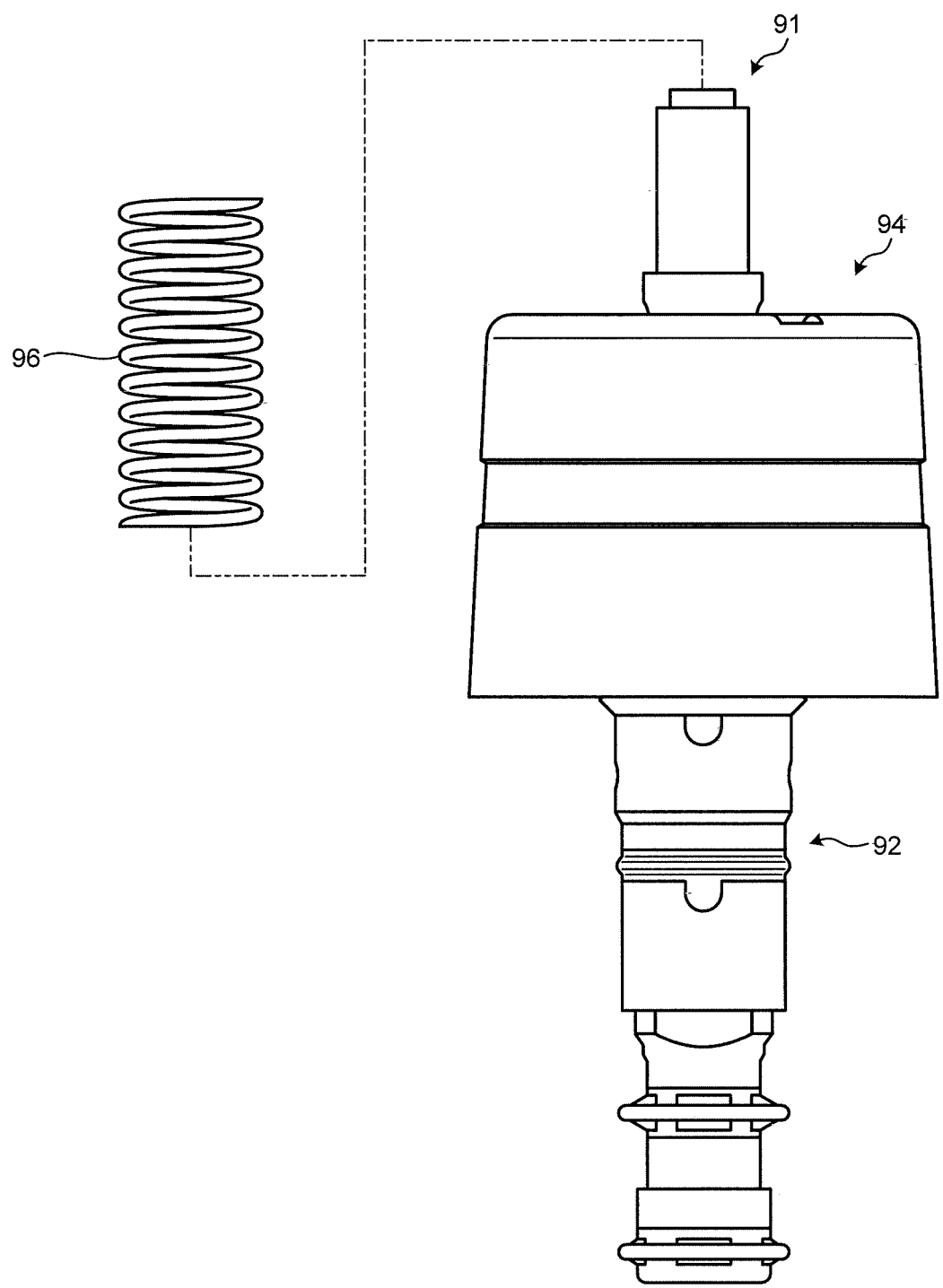
FIG. 33 is a view for explaining the assembly (part 3) of the air/water supply button.

After the structure 100B illustrated in FIG. 32 is obtained, the first coil spring 96 is attached to the shaft portion 91 (refer to FIG. 33). Accordingly, a structure 100C in which the first coil spring 96 is supported by the first member 92 is obtained (refer to FIG. 34).

Figure 34:
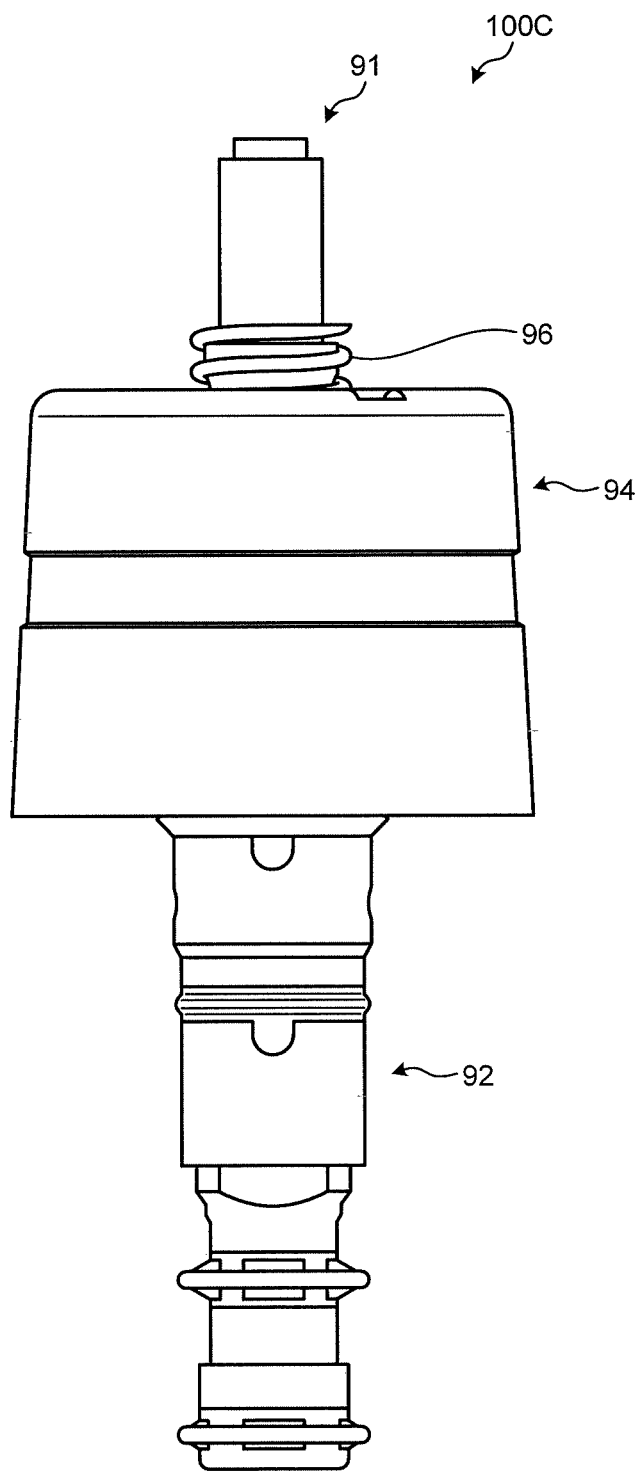
FIG. 34 is a view for explaining the assembly (part 3) of the air/water supply button.
Figure 35:
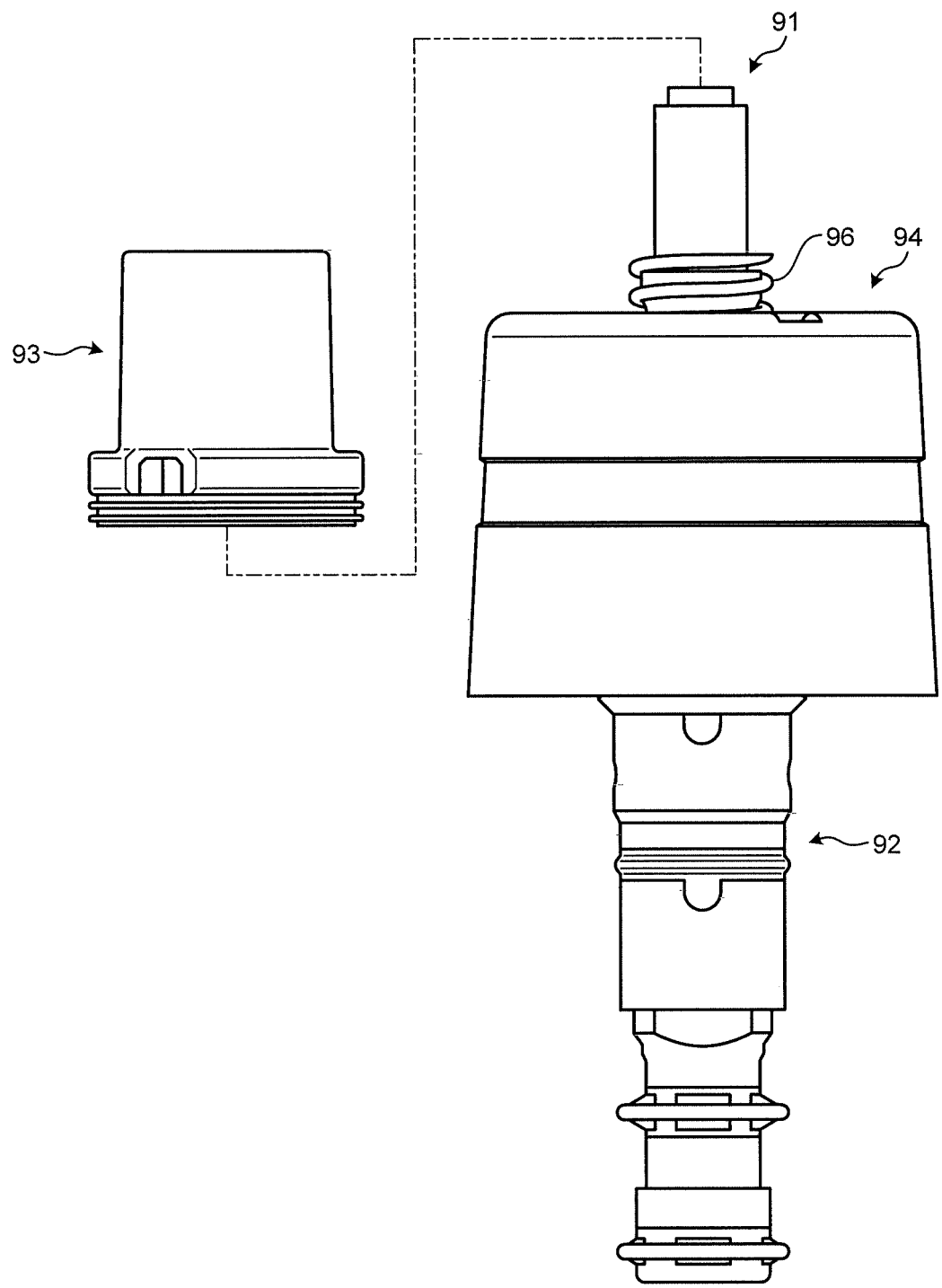
FIG. 35 is a view for explaining the assembly (part 4) of the air/water supply button.

After the structure 100C illustrated in FIG. 34 is obtained, the second member 93 is attached to the shaft portion 91 (refer to FIG. 35). Accordingly, a structure 100D which is supported by the first coil spring 96 and the first protrusions 9321a and 9321b abut the attachment member 94 is obtained (refer to FIG. 36).

Figure 36:
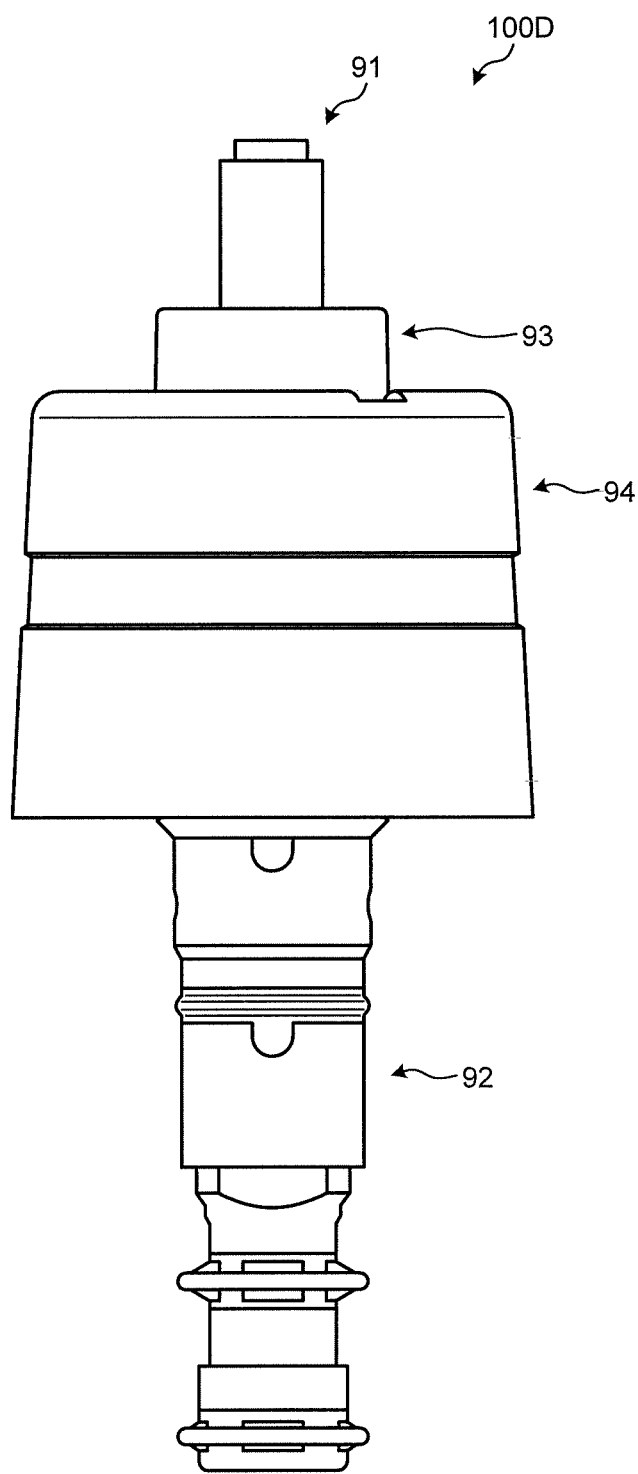
FIG. 36 is a view for explaining the assembly (part 4) of the air/water supply button.
Figure 37:
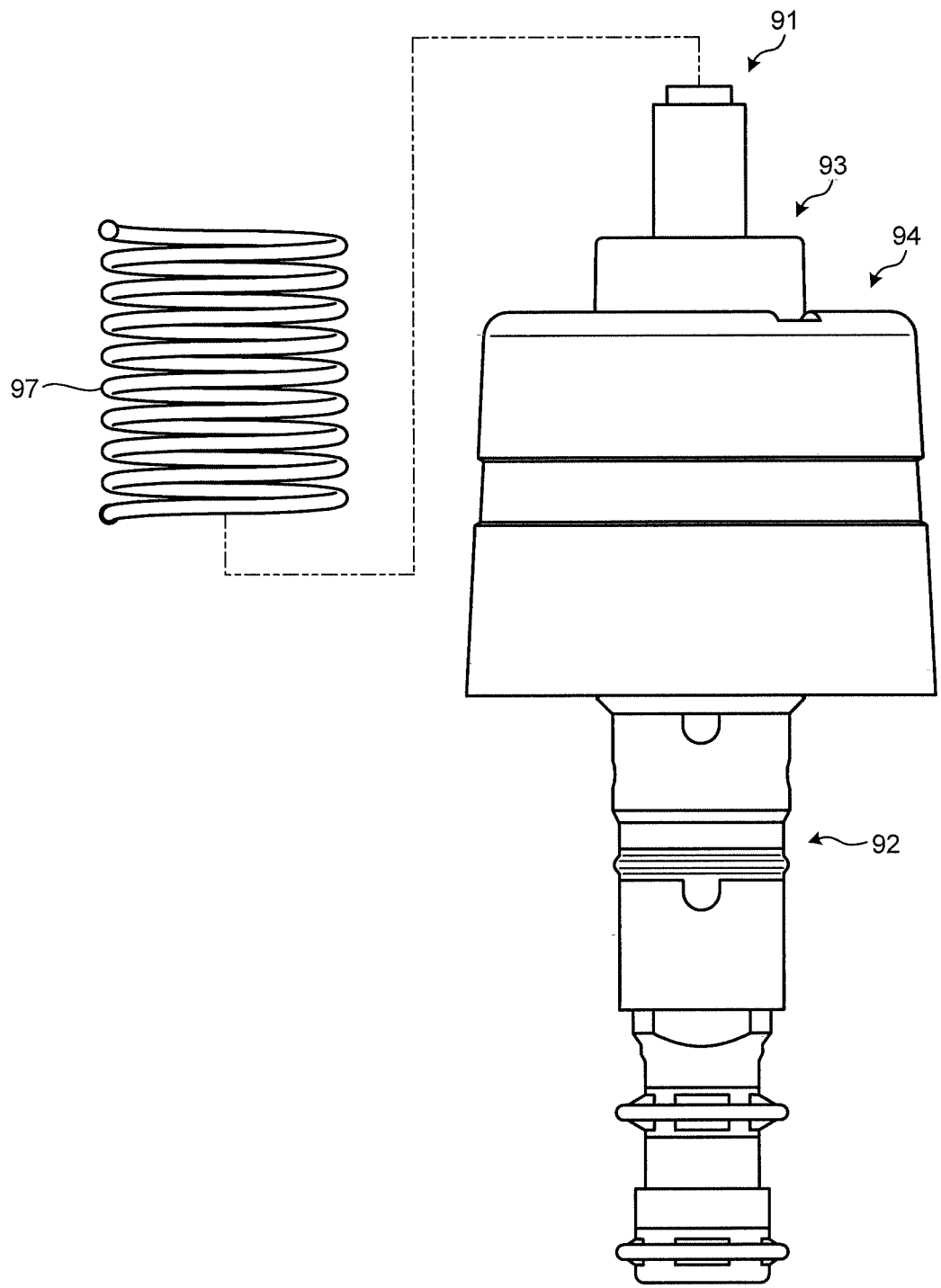
FIG. 37 is a view for explaining the assembly (part 5) of the air/water supply button.

After the structure 100D illustrated in FIG. 36 is obtained, the second coil spring 97 is attached to the shaft portion 91 (refer to FIG. 37). Accordingly, a structure 100E in which the second coil spring 97 is supported by the second member 93 is obtained (refer to FIG. 38).

Figure 38:
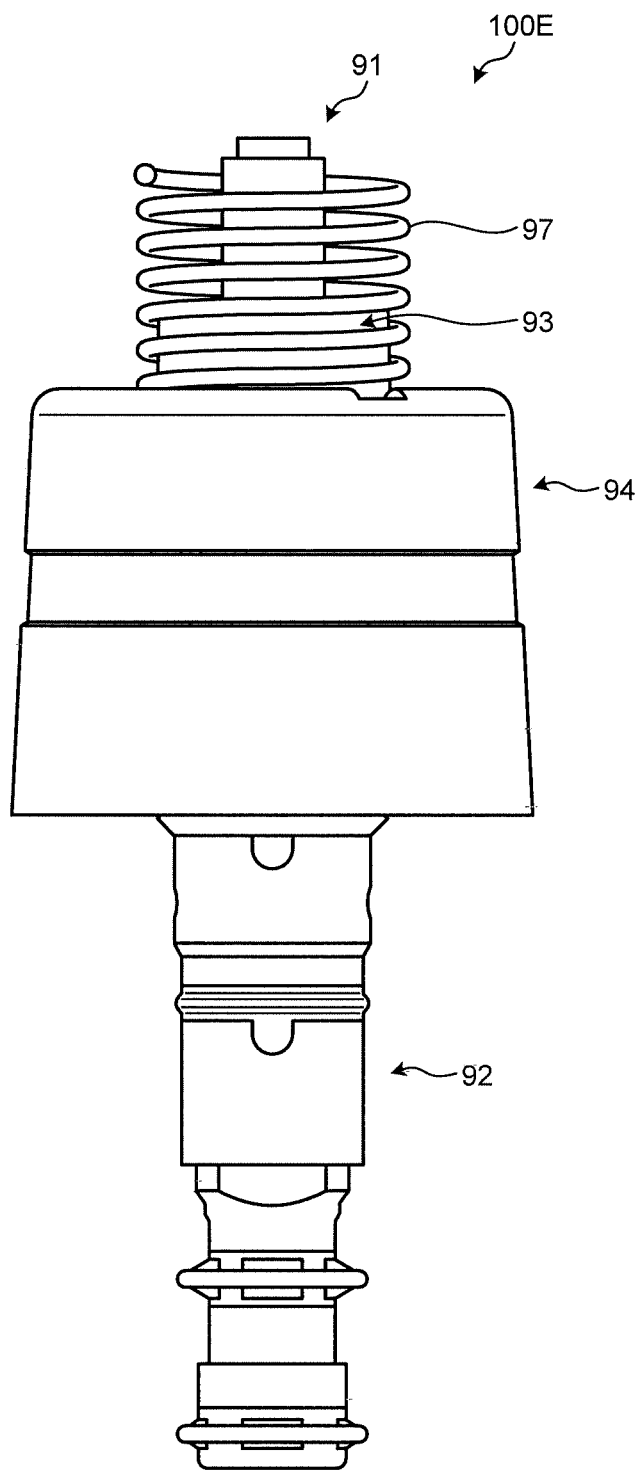
FIG. 38 is a view for explaining the assembly (part 5) of the air/water supply button.
Figure 39:
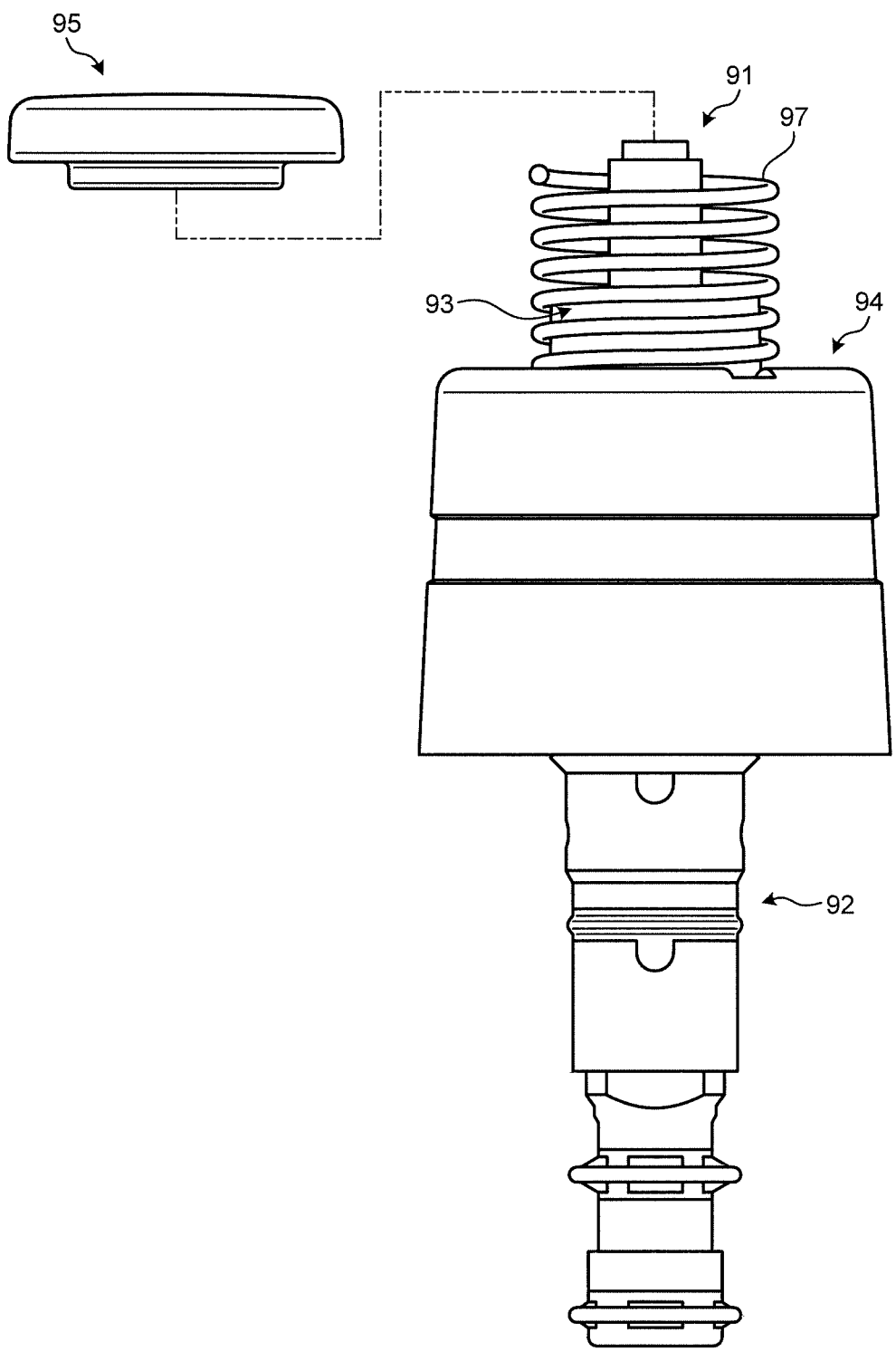
FIG. 39 is a view for explaining the assembly (part 6) of the air/water supply button.
Figure 40:
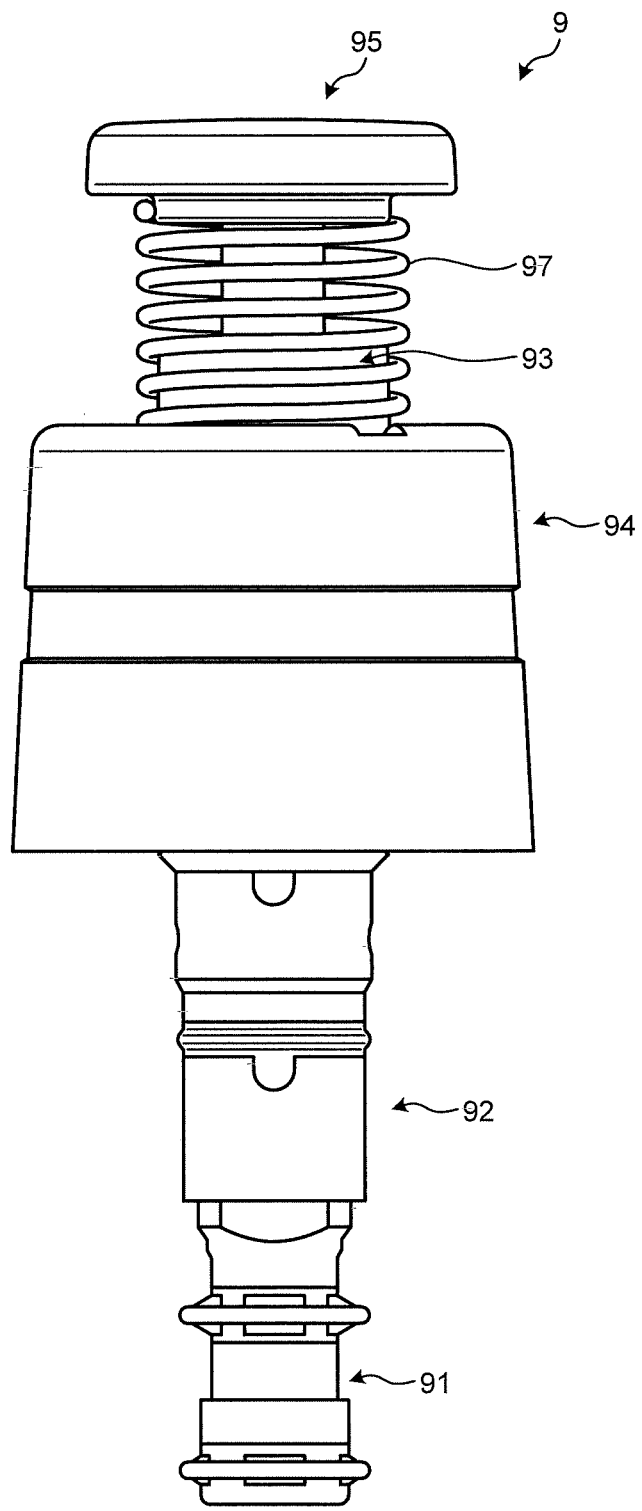
FIG. 40 is a view for explaining the assembly (part 6) of the air/water supply button.

After the structure 100E illustrated in FIG. 38 is obtained, the cap 95 is attached to an end portion of the shaft portion 91 (refer to FIG. 39). In this case, the shaft portion 91 and the cap 95 are fixed to each other by ultrasonic welding. Accordingly, the above-described air/water supply button 9 is obtained (refer to FIG. 40). In the air/water supply button 9, the central axes Ax2 to Ax6 of the respective members coincide with each other.

Next, connection states of the plurality of conduits 6 by the air/water supply button 9 will be described with reference to FIGS. 5 and 41 to 47. Hereinafter, a case where no operation is performed, a case where the leak hole 9522 is closed by a finger, a case where the pressing operation is performed in one step, and a case where the pressing operation is performed in two steps are described in this order.

Case Where No Operation is Performed

Figure 41:
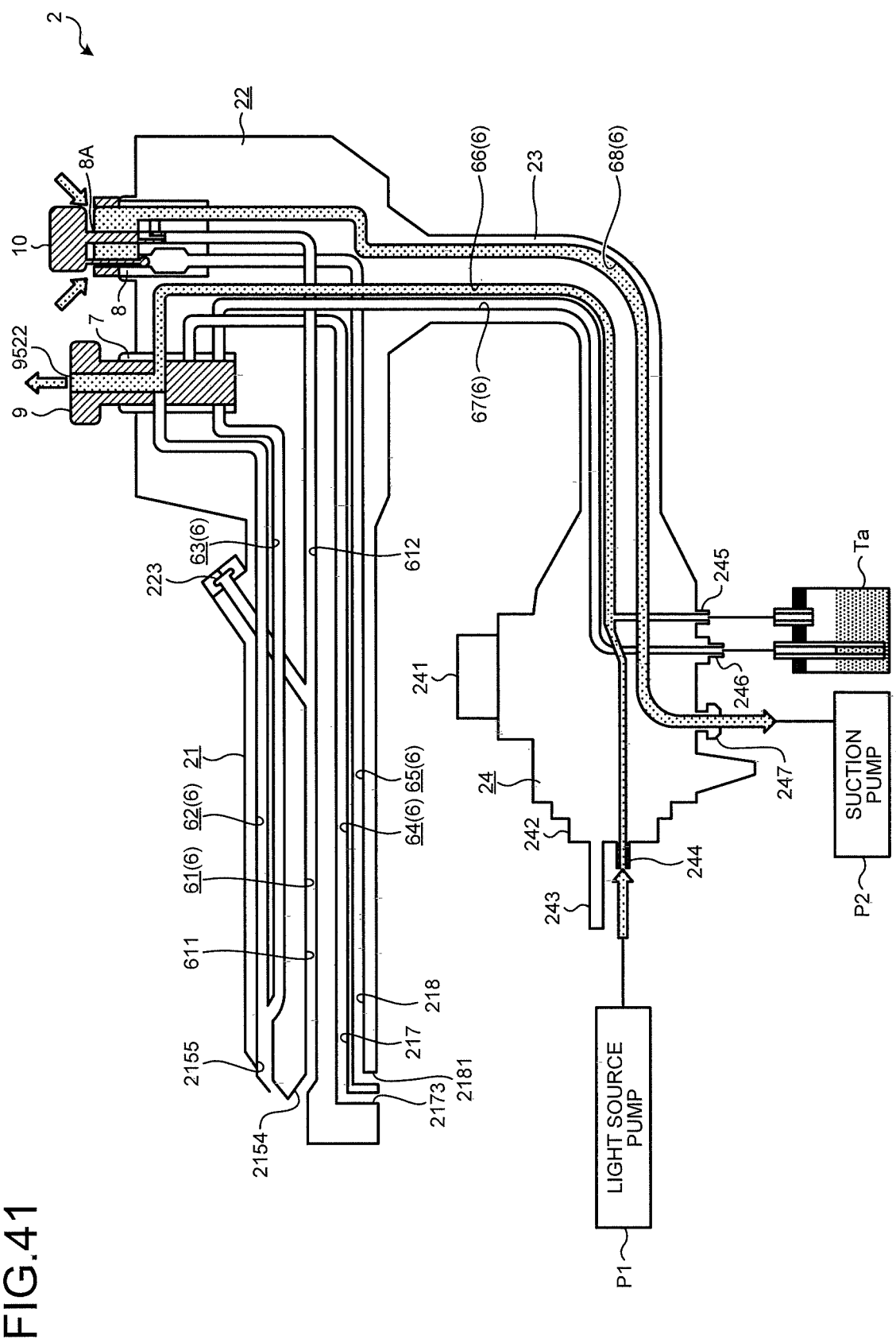
FIG. 41 is a view illustrating connection states of a plurality of conduits in a case where no operation is performed on the air/water supply button.

FIGS. 5 and 41 are views illustrating the connection states of the plurality of conduits 6 in the case where no operation is performed on the air/water supply button 9. Specifically, FIG. 41 illustrates the connection states of the plurality of conduits 6 by the air/water supply button 9. FIG. 41 is a view corresponding to FIG. 3.

In a case where no operation is performed on the air/water supply button 9, the air discharged from the light source pump P1 circulates toward the first cylinder 7 via the proximal end side first conduit 66. In addition, the air flowing toward the first cylinder 7 is discharged to the outside of the ultrasound endoscope 2 through a flow path of the communication passage 721—the first space A1—the communication hole 9212a—the second space A2—the communication hole 9111a—the first hole portion 9111—the leak hole 9522.

In addition, in the case where no operation is performed on the suction button 10, the air outside the ultrasound endoscope 2 flows into the second cylinder 8 via a leak gap 8A in the suction button 10 according to the driving of the suction pump P2, and is sucked into the suction pump P2 via the proximal end side third conduit 68.

That is, in the case of no operation, the distal end side first to fifth conduits 61 to 65 and the proximal end side first to third conduits 66 to 68 are not connected, and any one of the air supply, the water supply, and the suction from the distal end of the insertion portion 21 is not performed.

Case Where Leak Hole is Closed by Finger

Figure 42:
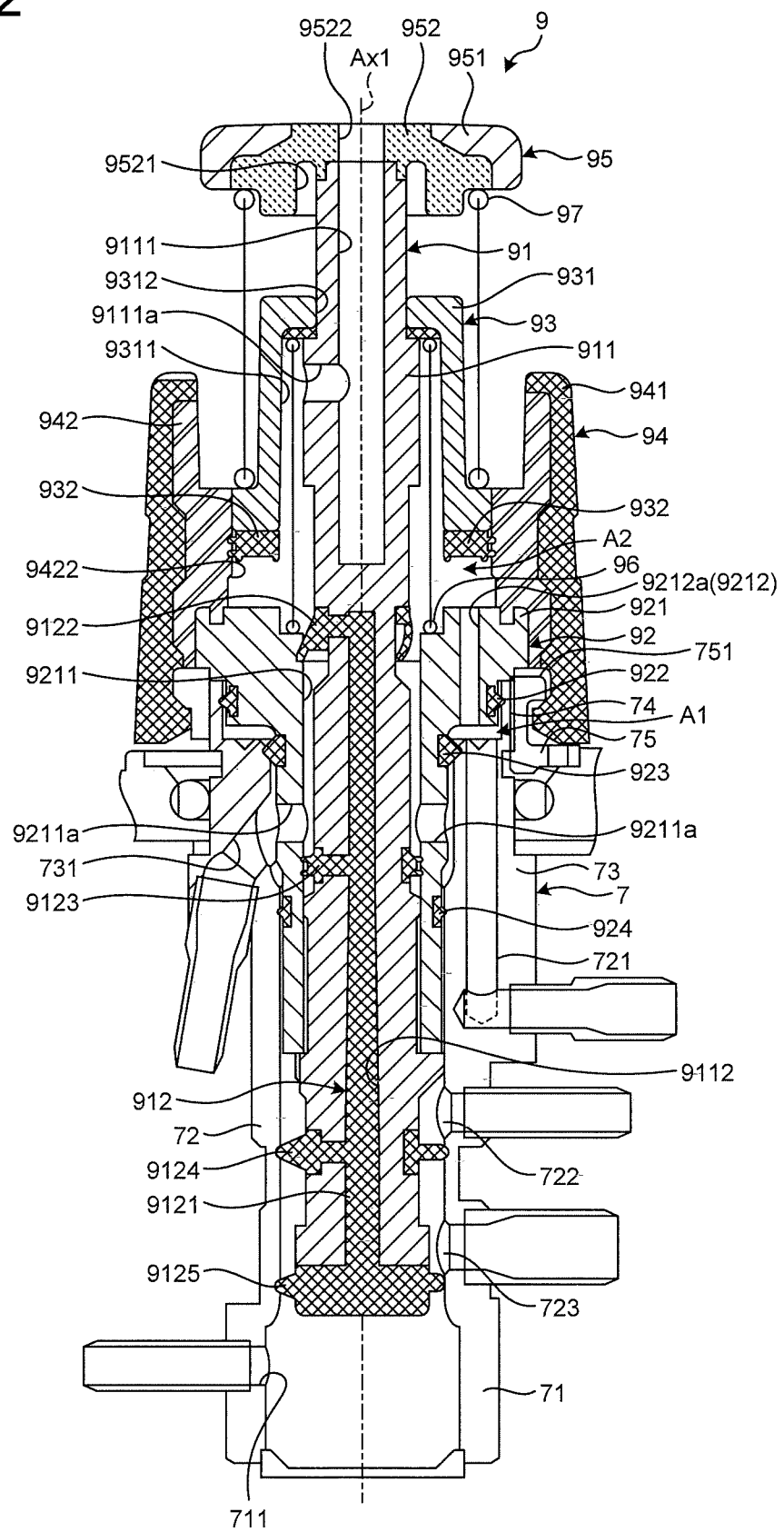
FIG. 42 is a view illustrating the connection states of the plurality of conduits in a case where a leak hole of the air/water supply button is blocked by a finger.
Figure 43:
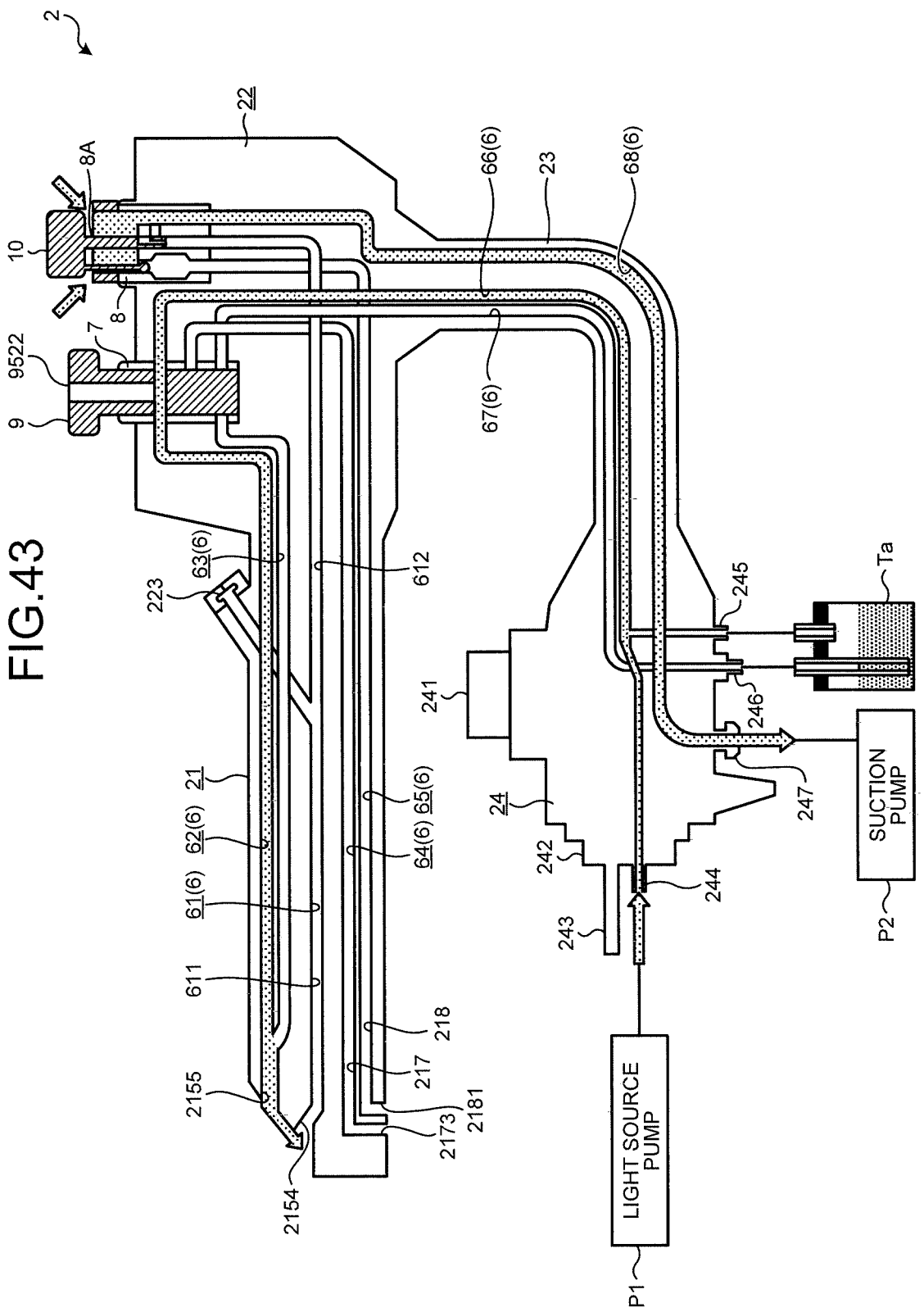
FIG. 43 is a view illustrating the connection states of the plurality of conduits in the case where the leak hole of the air/water supply button is blocked by a finger.

FIGS. 42 and 43 are views illustrating connection states of the plurality of conduits 6 in the case where the leak hole 9522 of the air/water supply button 9 is closed by a finger. Specifically, FIG. 42 corresponds to FIG. 5. FIG. 43 is a view corresponding to FIG. 3. Moreover, in FIG. 43, similarly to the case of FIG. 41, the suction button 10 is not operated at all.

In the case where the leak hole 9522 is closed by a finger, an air pressure in the first hole portion 9111 increases, and the check valve 9122 is deformed to the main body portion 911 side, and a space between the check valve 9122 and the first member 92 is opened. As a result, the air flowing into the first hole portion 9111 flows to the distal end side second conduit 62 through a flow path of the communication passage 721—the first space A1—the communication hole 9212a—the second space A2—the hollow space 9211—the communication hole 9211a—the communication passage 731. In addition, as illustrated in FIG. 43, the air flowing to the distal end side second conduit 62 is discharged from the air/water supply hole 2155 toward the objective optical system (not illustrated) in the capturing hole (not illustrated).

Case Where Pressing Operation is Performed in One Step

Figure 44:
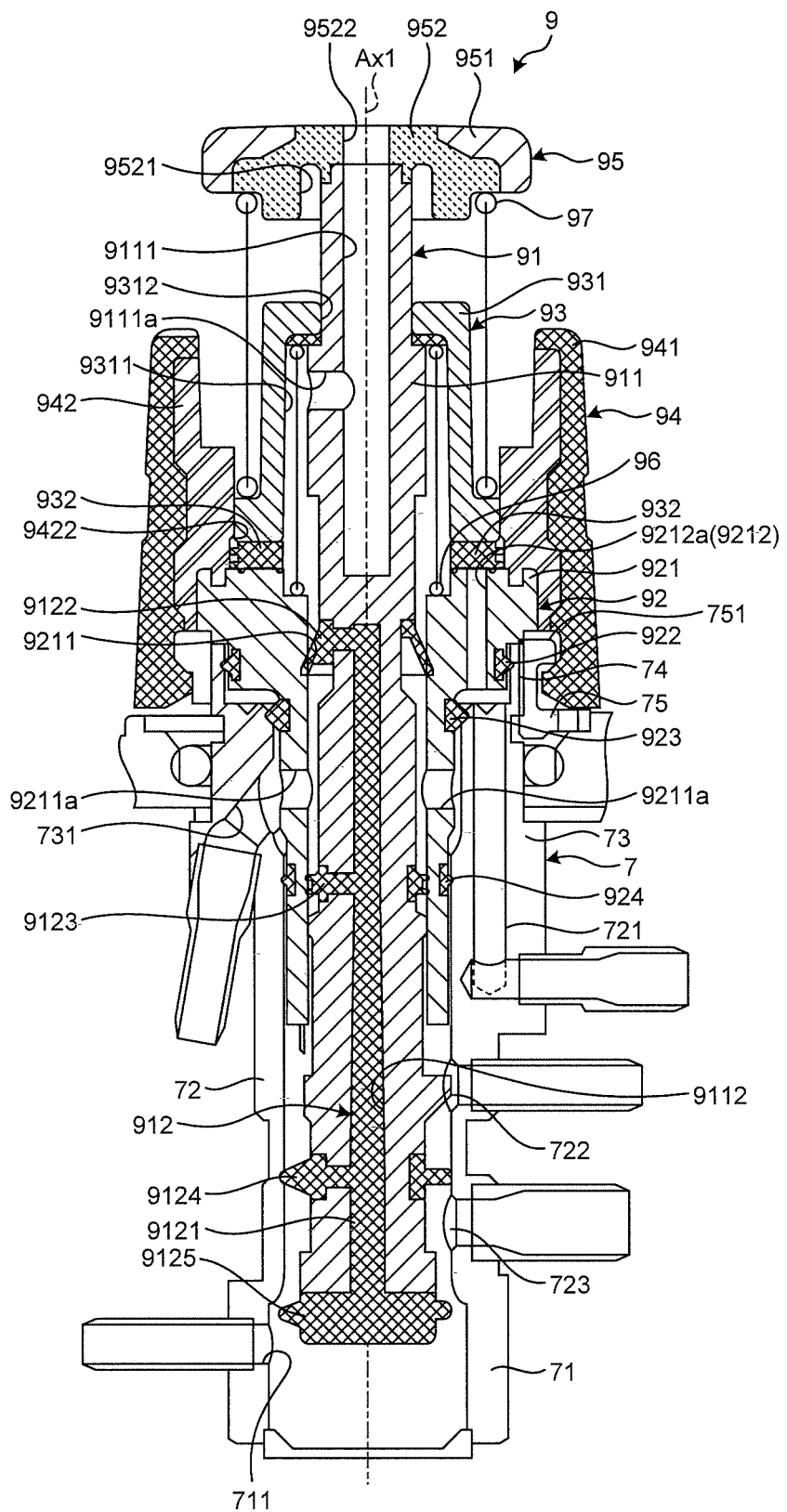
FIG. 44 is a view illustrating the connection states of the plurality of conduits in a case where a pressing operation is performed on the air/water supply button in one step.
Figure 45:
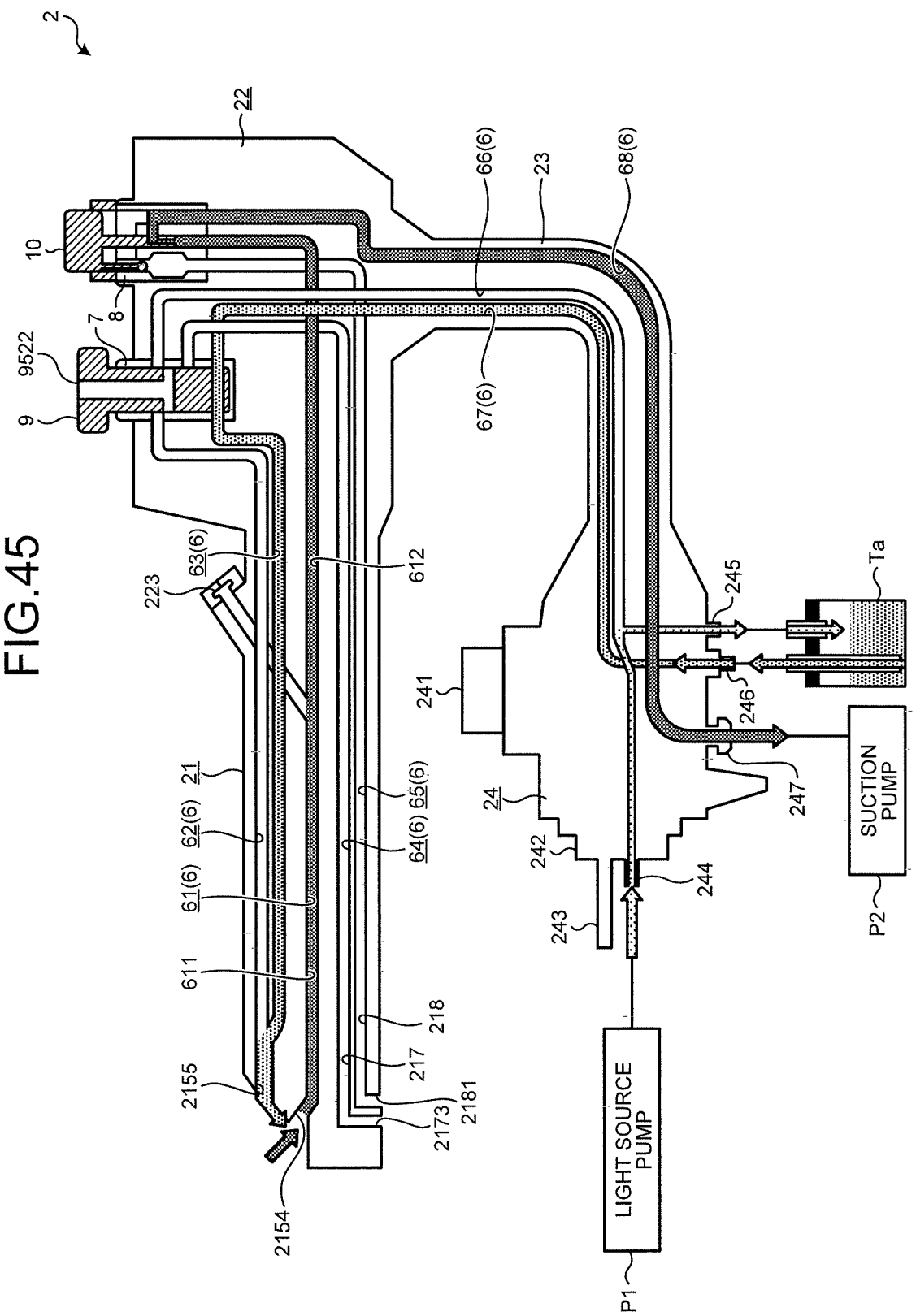
FIG. 45 is a view illustrating the connection states of the plurality of conduits in the case where the pressing operation is performed on the air/water supply button in one step.

FIGS. 44 and 45 are views illustrating connection states of the plurality of conduits 6 in the case where the pressing operation is performed on the air/water supply button 9 in one step. Specifically, FIG. 44 corresponds to FIG. 5. FIG. 45 is a diagram corresponding to FIG. 3.

In the case where the pressing operation is performed on the air/water supply button 9 in one step, only the first coil spring 96 is compressed by a magnitude relationship of the biasing forces of the first coil spring 96 and the second coil spring 97, and as illustrated in FIG. 44, the shaft portion 91, the second member 93, the cap 95, and the second coil spring 97 move downward integrally. In addition, when a lower surface of the seal member 932 of the second member 93 abuts an upper surface of the communication hole 9212a, the downward movements of the shaft portion 91, the second member 93, the cap 95, and the second coil spring 97 stop. That is, the communication hole 9212a is closed by the lower surface of the seal member 932. Therefore, as illustrated in FIG. 44, the air discharged from the light source pump P1 flows into the water supply tank Ta via the proximal end side first conduit 66, pressurizes the inside of the water supply tank Ta, and discharges water from the water supply tank Ta. In addition, the water from the water supply tank Ta flows toward first cylinder 7 via the proximal end side second conduit 67.

Here, according to the downward movement of the shaft portion 91, as illustrated in FIG. 44, the abutment between the protrusion portion 9125 and the inner peripheral surface of the sliding tubular portion 72 is released, and thus, the protrusion portion 9125 enters the lower end tubular portion 71. That is, in the first cylinder 7, the communication passages 711 and 723 communicate with each other. Accordingly, the water flowing to the first cylinder 7 flows to the distal end side third conduit 63 through a flow path of the communication passage 723—the lower end tubular portion 71—the communication passage 711. Moreover, the water flowing to the distal end side third conduit 63 is discharged from the air/water supply hole 2155 toward the objective optical system (not illustrated) in the capturing hole (not illustrated).

In addition, in the case where the pressing operation is performed on the suction button 10 in one step, the distal end side first conduit 61 and the proximal end side third conduit 68 are connected to (communicate with) each other via the suction button 10. In addition, the liquid in the subject flows from the treatment instrument channel 2154 into the distal end side first conduit 61, and is sucked to the suction pump P2 via the second cylinder 8 and the proximal end side third conduit 68. Moreover, in the case where the liquid in the subject is sucked from the treatment instrument channel 2154 in this manner, in order to close the treatment instrument insertion port 223 and apply the suction pressure to the distal end side (treatment instrument channel 2154 side), a forceps plug (not illustrated) is attached to the treatment instrument insertion port 223.

Case Where Pressing Operation is Performed in Two Steps

Figure 46:
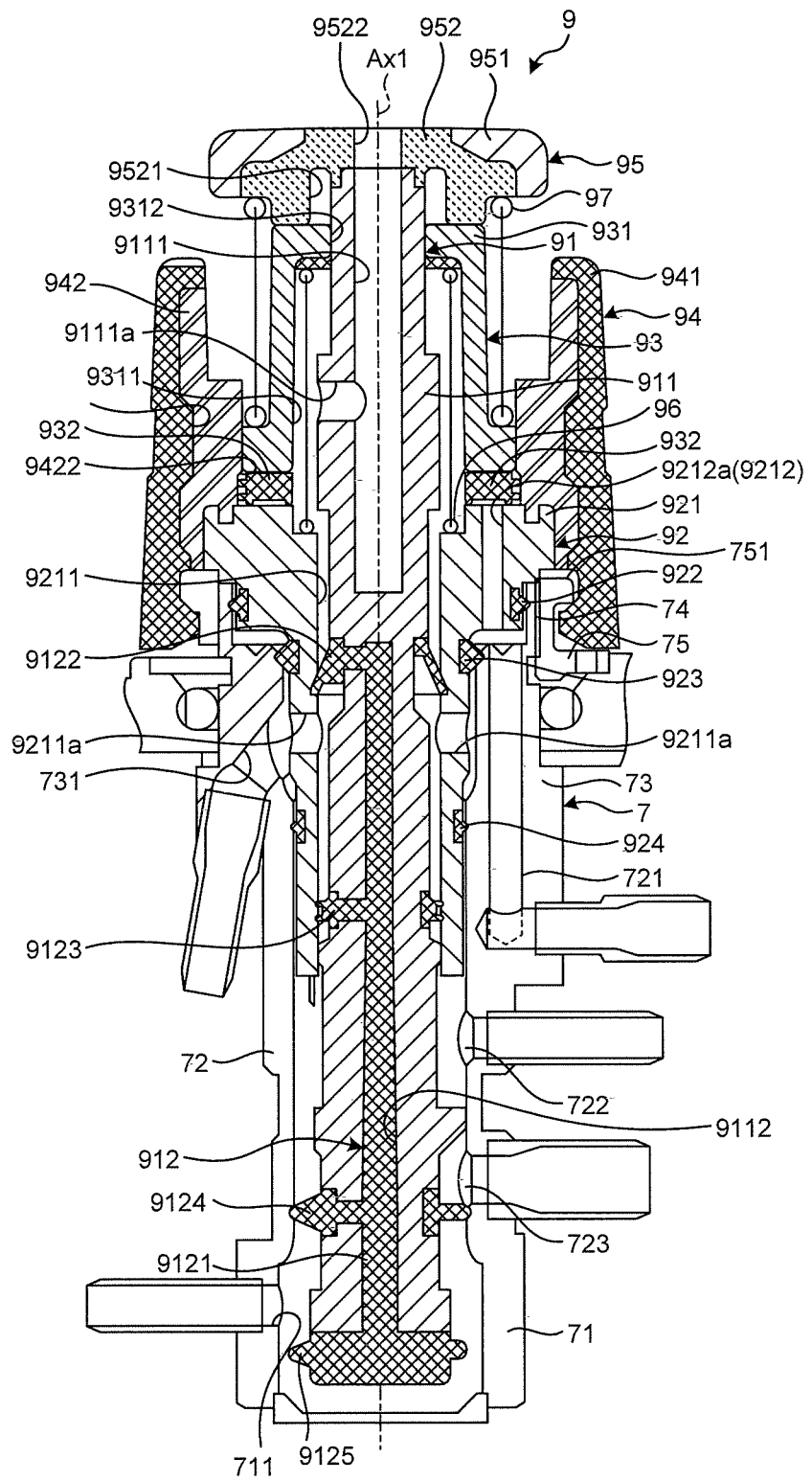
FIG. 46 is a view illustrating the connection states of the plurality of conduits in a case where the pressing operation is performed on the air/water supply button in two steps.
Figure 47:
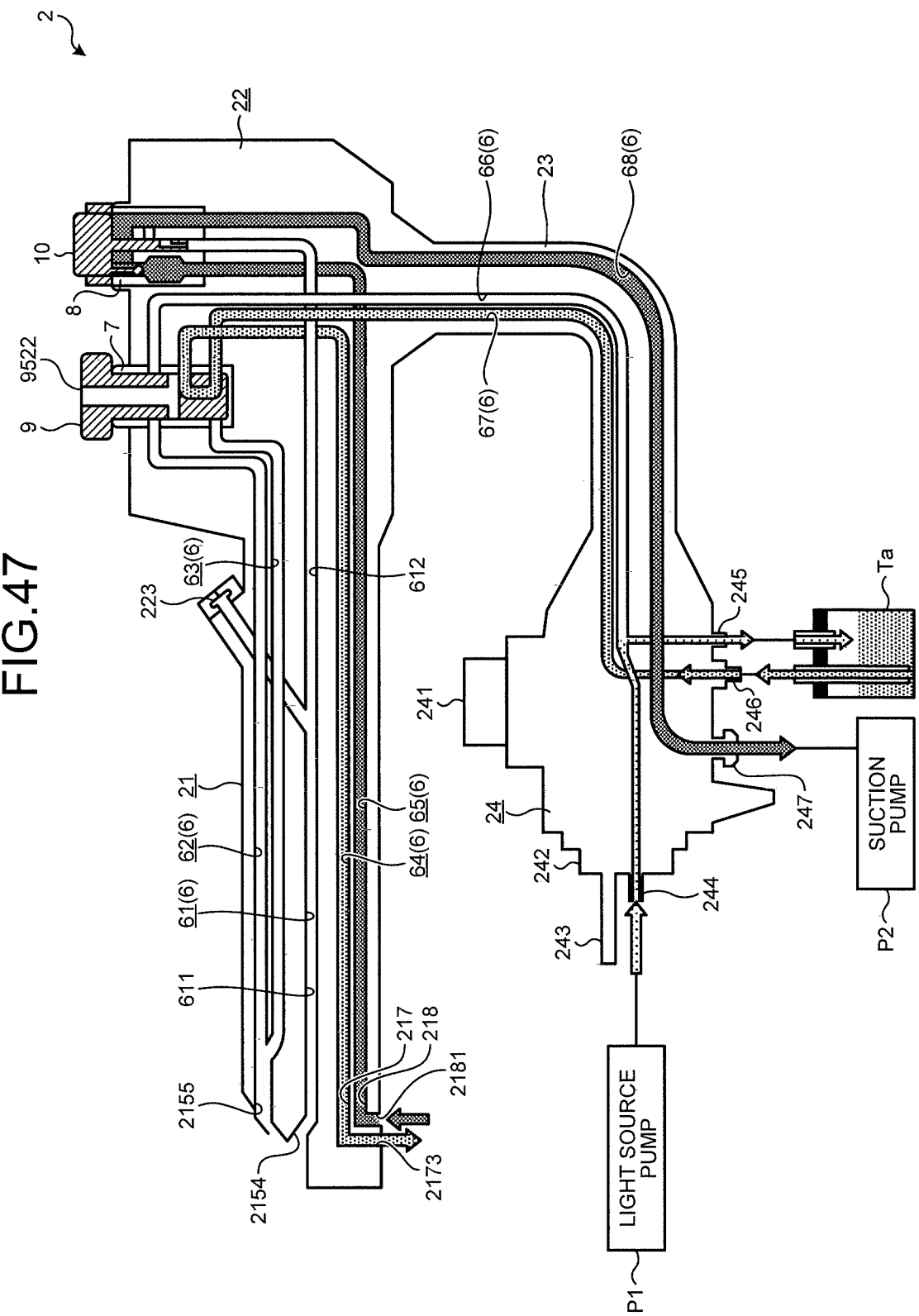
FIG. 47 is a view illustrating the connection states of the plurality of conduits in the case where the pressing operation is performed on the air/water supply button in two steps.

FIGS. 46 and 47 are views illustrating connection states of the plurality of conduits 6 in the case where the pressing operation is performed on the air/water supply button 9 in two steps. Specifically, FIG. 46 corresponds to FIG. 5. FIG. 47 is a view corresponding to FIG. 3.

In the case where the pressing operation is performed on the air/water supply button 9 in two steps (in a case where pressing operation is performed in one more steps from the state illustrated in FIG. 44), the second coil spring 97 is compressed, and as illustrated in FIG. 46, the second member 93 does not move, and the shaft portion 91, the first member 92, and the cap 95 integrally move downward. In addition, when a lower surface of the cap 95 abuts an upper surface of the second member 93, the downward movements of the shaft portion 91, the first member 92, and the cap 95 stop.

Here, according to the downward movement of the shaft portion 91, the exposed portion 9124b moves downward of the communication passage 723 inside the sliding tubular portion 72. That is, the communication passages 711 and 723 are separated from each other by the exposed portion 9124b, and the communication passages 722 and 723 communicate with each other. Accordingly, the water flowing to the first cylinder 7 flows to the distal end side fourth conduit 64 through a flow path of the communication passage 723—the communication passage 722. In addition, the water flowing to the distal end side fourth conduit 64 fills the balloon (not illustrated) via the scanning surface supply port 2173 as illustrated in FIG. 47.

Moreover, in the case where the pressing operation is performed on the suction button 10 in two steps, the distal end side fifth conduit 65 and the proximal end side third conduit 68 are connected to (communicate with) to each other via the suction button 10. In addition, the liquid (for example, water in the balloon) in the subject flows from the suction port 2181 into the distal end side fifth conduit 65 and is sucked into the suction pump P2 via the second cylinder 8 and the proximal end side third conduit 68. That is, the distal end side fifth conduit 65 (suction hole 218) has a function as a suction conduit according to the present disclosure.

The air/water supply button 9 according to the present embodiment has a configuration in which a first coil spring 96 and a second coil spring 97 are connected in series. In other words, in the air/water supply button 9, the first coil spring 96 and the second coil spring 97 have a structure in which the load applied by one of the first coil spring 96 and the second coil spring 97 is received by the other thereof via the second member 93. As described above, in the case where the shaft portion 91 is pushed in two steps, it is preferable to provide a change in an amount of operating force such that pushing in a first step and pushing in a second step may be identified. In this case, the two coil springs are connected to each other in series, and thus, it is possible to independently design a load applied to the pushing in the first step and a load applied to the pushing in the second step. That is, an ability of the first coil spring 96 and an ability of the second coil spring 97 may be designed in accordance with an ability of the related pushing. Accordingly, it is possible to easily perform the ability when the pushing is performed in two steps.

In the embodiment described above, in the seal portion 9321 for airtightly or watertightly sealing a portion between the attachment member 94 and the seal portion 9321, the length $d_5$ of each of the first protrusions 9321a and 9321b in the direction orthogonal to the central axis Ax4, the maximum length $d_6$ of the first protrusion 9321a in the central axis Ax4 direction, the distance $d_7$ between the first protrusion 9321a and the first protrusion 9321b, and the shrinkage amount $d_8$ of each of the first protrusions 9321a and 9321b when the first protrusions 9321a and 9321b come into pressure-contact with the pressure-contact object satisfy the relationships of $d_6 \leq d_5$, $2d_6 \leq d_7$, and $d_8 < d_5$. As a result, in a case where the contact position is changed in the state where the first protrusions 9321a and 9321b are in contact with the pressure-contact object, the first protrusions 9321a and 9321b are deformed so as to fall down, and the amount of operating force may be reduced while the contact state is maintained. According to the present embodiment, it is possible to easily perform the pushing into the cylinder while securing the air tightness or water tightness. Depending on the inclination angles of the first protrusions 9321a and 9321b, the above-described effect may be obtained even if $2d_6 \leq d_7$ is not satisfied.

Moreover, in the above-described embodiment, the inner peripheral surface 9422 facing the first protrusions 9321a and 9321b of the seal portion 9321 includes the first inner peripheral surface 9422a which is provided according to the position where the flow path is switched, the second inner peripheral surface 9422b having the diameter in the direction orthogonal to the central axis Ax5 which is larger than the diameter formed by the first inner peripheral surface 9422a, and the inclination surface 9422c which connects the first inner peripheral surface 9422a and the second inner peripheral surface 9422b to each other. As a result, when the shaft portion 91 is pushed in, it is possible to increase the difference in the amount of operating force when the flow path is switched while air tightness or water tightness is secured.

Hereinbefore, the embodiment for carrying out the present disclosure is described. However, the present disclosure should not be limited only by the above-described embodiment. For example, in the inner peripheral surface 9422, it is described that the diameter of the inner periphery is changed in accordance with a switching position of the flow path. However, a uniform diameter of the inner periphery may be provided as long as it is possible to provide a difference in the amount of the operating force so that the user may recognize a boundary between the first step and the second step. In addition, the present disclosure is not limited to the inclination surface 9422c, and the first inner peripheral surface 9422a and the second inner peripheral surface 9422b may be connected by a surface of which diameter is changed stepwise such as a surface of which diameter is changed every predetermined distance in the central axis Ax5 direction.

In addition, in the endoscope air/water supply valve (air/water supply button 9) according to the above-described embodiment, the structure is adopted in which the connection states of the plurality of conduits 6 are switched by the two-step pressing operation is used. However, the present disclosure is not limited to this, and a structure which may be performed by only the one-step pressing operation may be adopted.

Further, in the above-described embodiment, the endoscope system 1 is described as having both the function of generating the ultrasound image and the function of generating the endoscope image. However, the present disclosure is not limited to this, and a configuration having only the function of generating the ultrasound image may be adopted.

Moreover, in the above-described embodiment, the endoscope system 1 is not limited to a medical field, and may be an endoscope system that observes an inside of a subject such as a machine structure in an industrial field.

Thus, the present disclosure may include various embodiments within a scope which does not depart from a technical concept described in the claims.

As described above, the endoscope air/water supply valve and the endoscope according to the present disclosure are useful for easily performing the pushing into the cylinder while securing the air tightness or water tightness.

According to the present disclosure, it is possible to easily perform the pushing into the cylinder while securing the air tightness or water tightness.

The above and other features, advantages and technical and industrial significance of this disclosure will be better understood by reading the following detailed description of presently preferred embodiments of the disclosure, when considered in connection with the accompanying drawings.

What is claimed is:

1. An endoscope valve for switching connection states of a plurality of conduits formed in an endoscope, the endoscope valve comprising:
   a piston portion having a rod shape extending along a central axis; and
   an attachment member including a surface forming a hollow space extending in a central axis direction, the attachment member being attachable to the endoscope,
   wherein the piston portion is inserted into the attachment member and includes:
      a plurality of protrusions protruding in a direction perpendicular to the central axis and abutting a surface forming the hollow space of the attachment member; and
      a seal portion having an annular portion with the central axis of the piston portion as a symmetry axis and configured to seal a portion between the attachment member and the seal portion, and
   in the plurality of protrusions, when a length of the protrusion in a protrusion direction is indicated by $d_A$, a length of the protrusion in the central axis direction is indicated by $d_B$, and a shrinkage amount of the protrusion when the protrusion comes into pressure-contact with a pressure-contact object is indicated by $d_C$, relationships of $d_B < d_A$ and $d_C < d_A$ are satisfied.

2. The endoscope valve according to claim 1, wherein a free end of the protrusion is deformable relative to a base end of the protrusion.

3. The endoscope valve according to claim 1,
wherein the piston portion is stepwise switchable to any one of a plurality of flow paths formed by the piston portion and a portion of the plurality of conduits, according to a position in the endoscope,
the plurality of flow paths includes
   a first flow path through which a gas discharged from a distal end of the endoscope flows,
   a second flow path through which a liquid discharged from the distal end of the endoscope flows, and
   a third flow path which leads to an inside of a balloon attached to the endoscope, and
the first flow path, the second flow path, and the third flow path are switched in this order according to a push-in amount of the endoscope valve with respect to the endoscope.

4. The endoscope valve according to claim 1, wherein when a distance between the protrusions adjacent to each other in the central axis direction is indicated by $d_D$, a relationship of $2d_B \leq d_D$ is further satisfied.

5. The endoscope valve according to claim 1,
wherein the piston portion further includes
   a shaft extending in a rod shape,
   a tubular portion attached to the shaft and having a tubular shape into which a portion of the shaft is inserted, and
   a first elastic body configured to bias the tubular portion such that the tubular portion moves to one end side of the shaft, and
the seal portion is provided in the tubular portion.

6. The endoscope valve according to claim 5, further comprising:
   a cap connected to one end of the shaft and including a leak hole through which a gas flowing via the conduit is dischargeable; and
   a second elastic body provided between the tubular portion and the cap and configured to bias the tubular portion and the cap in a direction in which the tubular portion and the cap are away from each other.

7. The endoscope valve according to claim 1,
wherein a surface of the attachment member facing the plurality of protrusions includes
   a first inner peripheral surface which is axially symmetrical to a central axis of the attachment and has a diameter smaller than diameters of distal ends of the plurality of protrusions,
   a second inner peripheral surface which is axially symmetrical to the central axis of the attachment member and has a diameter equal to or larger than the diameters of the distal ends of the plurality of protrusions, and
   a connection surface which is axially symmetrical to the central axis of the attachment member and connects the first inner peripheral surface and the second inner peripheral surface to each other.

8. An endoscope comprising:
the endoscope valve according to claim 1; and
a cylinder communicating with each of the plurality of conduits and holding the endoscope valve in a forward or rearward movable manner.

* * * * *